United States Patent
Feng

(10) Patent No.: US 9,889,123 B2
(45) Date of Patent: Feb. 13, 2018

(54) POLYMORPHS OF DEUTERATED OMEGA-DIPHENYLUREA OR SALTS THEREOF

(71) Applicant: Suzhou Zelgen Biopharmaceuticals Co., Ltd., Jiangsu (CN)

(72) Inventor: Weidong Feng, Jiangsu (CN)

(73) Assignee: Suzhou Zelgen Biopharmaceutical Co., Ltd., Jiangsu (CN)

( * ) Notice: Subject to any disclaimer, the term of this patent is extended or adjusted under 35 U.S.C. 154(b) by 8 days.

(21) Appl. No.: 15/414,813

(22) Filed: Jan. 25, 2017

(65) Prior Publication Data

US 2017/0128427 A1     May 11, 2017

Related U.S. Application Data

(62) Division of application No. 14/415,340, filed as application No. PCT/CN2013/079469 on Jul. 16, 2013, now Pat. No. 9,573,900.

(30) Foreign Application Priority Data

Jul. 18, 2012 (CN) ............... 2012 1 0249796

(51) Int. Cl.
    *A61K 31/44*     (2006.01)
(52) U.S. Cl.
    CPC ................... *A61K 31/44* (2013.01)
(58) Field of Classification Search
    CPC .................. C07D 213/81; A61K 31/44
    USPC ........................................... 514/355
    See application file for complete search history.

(56) References Cited

U.S. PATENT DOCUMENTS

| | | | |
|---|---|---|---|
| 8,618,306 B2 | 12/2013 | Feng et al. |
| 8,669,369 B2 | 3/2014 | Feng et al. |
| 8,748,666 B2 | 6/2014 | Gao et al. |
| 8,759,531 B2 | 6/2014 | Feng et al. |
| 9,072,796 B2 | 7/2015 | Feng et al. |
| 9,078,933 B2 | 7/2015 | Feng et al. |
| 2009/0069388 A1 | 3/2009 | Czarnik |
| 2009/0192200 A1 | 7/2009 | Gavenda et al. |
| 2009/0215833 A1 | 8/2009 | Grunenberg et al. |
| 2013/0012548 A1 | 1/2013 | Xing et al. |
| 2013/0018209 A1 | 1/2013 | Gao et al. |
| 2013/0035492 A1 | 2/2013 | Feng et al. |
| 2013/0060043 A1 | 3/2013 | Feng et al. |
| 2013/0060044 A1 | 3/2013 | Feng et al. |

(Continued)

FOREIGN PATENT DOCUMENTS

| | | |
|---|---|---|
| CN | 101671299 A | 3/2010 |
| CN | 101676266 A | 3/2010 |

(Continued)

OTHER PUBLICATIONS

Int'l Search Report dated Oct. 24, 2013 in Int'l Application No. PCT/CN2013/079469.

*Primary Examiner* — Daniel R Carcanague
(74) *Attorney, Agent, or Firm* — Panitch Schwarze Belisario & Nadel LLP

(57) ABSTRACT

The invention relates to polymorphs of deuterated omega-diphenylurea or salts thereof. In particular, the invention provides polymorphs of 4-(4-{3-[4-chloro-3-(trifluoromethyl)phenyl]-ureido]-phenoxy}-2-(N-1',1',1'-trideuteromethyl)picolinamide or its salt, namely, polymorphs of the compound as shown in formula (I) or its salt. The polymorphs are suited for preparing the pharmaceutical composition used for inhibiting phosphokinase (such as raf kinases).

7 Claims, 11 Drawing Sheets

(56) References Cited

U.S. PATENT DOCUMENTS

| | | |
|---|---|---|
| 2014/0088311 A1 | 3/2014 | Feng et al. |
| 2014/0128612 A1 | 5/2014 | Feng et al. |
| 2015/0175545 A1 | 6/2015 | Feng et al. |

FOREIGN PATENT DOCUMENTS

| | | |
|---|---|---|
| WO | 0041698 A1 | 7/2000 |
| WO | 2011076711 A2 | 6/2011 |
| WO | 2011113367 A1 | 9/2011 |
| WO | 2012071425 A1 | 5/2012 |

POLYMORPHS OF DEUTERATED OMEGA-DIPHENYLUREA OR SALTS THEREOF

CROSS REFERENCE TO RELATED APPLICATION

This application is a divisional of U.S. patent application Ser. No. 14/415,340, filed on Jan. 16, 2015, entitled "POLYMORPHS OF DEUTERATED OMEGA-DIPHENYLUREA OR SALTS THEREOF," which is a Section 371 of International Application No. PCT/CN2013/079469, filed Jul. 16, 2013, which was published in the Chinese language on Jan. 23, 2014, under International Publication No. WO 2014/012480 A1, the disclosure of which is incorporated herein by reference.

TECHNICAL FIELD

The present invention relates to the field of medicine, and particularly, relates to polymorphs of deuterated omega-diphenylurea or salts thereof, and more particularly, relates to polymorphs of 4-(4-{3-[4-chloro-3-(trifluoromethyl)phenyl)-ureido]-phenoxy}-2-(N-1',1',1'-trideutero-methyl)pico linamide or salts thereof.

BACKGROUND

The structure of 4-(4-{3-[4-chloro-3-(trifluoromethyl) phenyl)-ureido]-phenoxy}-2-(N-1',1',1'-trideutero-methyl) picolinamide is shown as formula I.

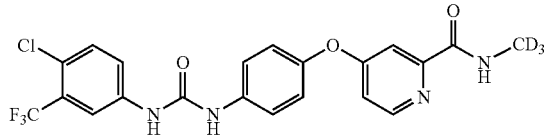

I

The compound of formula I, with a molecular formula of $C_{21}H_{13}D_3ClF_3N_4O_3$ and a molecular weight of 467.84, is a white or off-white crystal powder, odorless and tasteless. It is very soluble in dimethyl sulfoxide or dimethyl formamide, sparingly soluble in methanol, slightly soluble in acetone, anhydrous ethanol and glacial acetic acid, and practically insoluble in water.

The compound of formula I belongs to compounds that inhibit raf kinase, and is suitable for preparing drugs for the treatment of cancer and other related diseases. Different crystal forms of a drug might affect its dissolution, absorption in vivo, thereby affecting its clinical therapeutic effect and safety to a certain extent. In particular, for some slightly soluble solid or semisolid oral preparations, the influence of crystal forms is huge. There are no studies on polymorphs of compound I up to now, and no polymorphs of compound I have been developed yet.

Therefore, it is necessary to develop the polymorphs of compound I.

SUMMARY OF INVENTION

The purpose of the present invention is to provide polymorphs of compound I or pharmaceutically acceptable salts thereof, or solvates thereof.

In the first aspect, polymorphs of compound I or pharmaceutically acceptable salts thereof, or solvates thereof is provided,

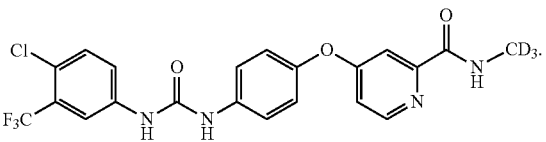

I

In another embodiment, the pharmaceutically acceptable salt is a p-toluenesulfonate.

In another embodiment, in p-toluenesulfonate of compound I, the molar ratio of compound I and p-toluenesulfonic acid is 1:1 or 2:1.

In another embodiment, the solvate is methanol or ethanol solvate of the p-toluenesulfonate of compound I.

In another embodiment, the polymorph is polymorph I of the 1/1 p-toluenesulfonate of compound I (1:1), wherein polymorph I has 1 to 3 characteristic peaks in X-ray powder diffraction pattern selected from the group consisting of 13.182±0.2°, 21.472±0.2° and 22.833±0.2°.

In another embodiment, polymorph I further has one or more characteristic peaks in X-ray powder diffraction pattern selected from the group consisting of 4.397±0.2°, 16.636±0.2°, 17.821±0.2°, 20.407±0.2° and 20.782±0.2°.

In another embodiment, polymorph I has characteristic peaks in X-ray powder diffraction as essentially shown in FIG. 1a.

In another embodiment, polymorph I has a maximum peak of 231.5-237.7° C. in differential scanning calorimetry pattern.

In another embodiment, polymorph I has a differential scanning calorimetry pattern as essentially shown in FIG. 1b.

In another embodiment, in polymorph I, the molar ratio of compound I and p-toluenesulfonic acid is 1:1.

In another embodiment, the polymorph is polymorph II of methanol solvate of the 1/1 p-toluenesulfonate of compound I (1:1:1), wherein polymorph II has 1 to 3 characteristic peaks in X-ray powder diffraction pattern selected from the group consisting of 21.014±0.2°, 18.333±0.2° and 25.301±0.2°.

In another embodiment, polymorph II further has one or more characteristic peaks in X-ray powder diffraction pattern selected from the group consisting of 8.405±0.2°, 15.906±0.2°, 19.477±0.2° and 24.744±0.2°.

In another embodiment, polymorph II has characteristic peaks in X-ray powder diffraction pattern as essentially shown in FIG. 2a.

In another embodiment, polymorph II has maximum peaks of 193.5-197.0° C. and 228.6-236.4° C. in differential scanning calorimetry pattern.

In another embodiment, polymorph II of the methanol solvate has a differential scanning calorimetry pattern as essentially shown in FIG. 2b.

In another embodiment, in polymorph II, the molar ratio of compound I, p-toluenesulfonic acid and methanol is 1:1:1.

In another embodiment, the polymorph is polymorph III of the 1/1 p-toluenesulfonate of compound I (1:1), wherein polymorph III has 1 or 2 characteristic peaks in X-ray powder diffraction pattern selected from the group consisting of 19.858±0.2° and 25.896±0.2°.

In another embodiment, polymorph III further has one or more characteristic peaks in X-ray powder diffraction pattern selected from the group consisting of 17.726±0.2°, 19.325±0.2° and 21.575±0.2°.

In another embodiment, polymorph III has characteristic peaks in X-ray powder diffraction pattern as essentially shown in FIG. 3a.

In another embodiment, polymorph III has maximum peaks of 193.8-197.2° C. and 231.3-236.9° C. in differential scanning calorimetry pattern.

In another embodiment, polymorph III has a differential scanning calorimetry pattern as essentially shown in FIG. 3b.

In another embodiment, in polymorph III, the molar ratio of compound I to p-toluenesulfonic acid is 1:1.

In another embodiment, the polymorph is polymorph IV of ethanol solvate of the 1/1 p-toluenesulfonate of compound I (1:1:1), wherein polymorph IV has 1 or 2 characteristic peaks in X-ray powder diffraction pattern selected from the group consisting of 20.961±0.2° and 18.277±0.2°.

In another embodiment, polymorph IV further has one or more characteristic peaks in X-ray powder diffraction pattern selected from the group consisting of 9.273±0.2°, 15.812±0.2°, 24.674±0.2°, 25.246±0.2° and 27.552±0.2°.

In another embodiment, polymorph IV has characteristic peaks in X-ray powder diffraction pattern as essentially shown in FIG. 4a.

In another embodiment, polymorph IV has maximum peaks of 190.8-192.5° C. and 230.0-237.4° C. in differential scanning calorimetry pattern.

In another embodiment, polymorph IV has a differential scanning calorimetry pattern as essentially shown in FIG. 4b.

In another embodiment, in polymorph IV, the molar ratio of compound I, p-toluenesulfonic acid and ethanol is 1:1:1.

In another embodiment, the polymorph is polymorph V of the 1/2 p-toluenesulfonate of compound I (2:1), wherein polymorph V has one or more characteristic peaks in X-ray powder diffraction pattern selected from the group consisting of 13.423±0.2°, 13.974±0.2°, 20.467±0.2°, 20.705±0.2°, 24.929±0.2° and 27.101±0.2°.

In another embodiment, polymorph V further has one or more characteristic peaks in X-ray powder diffraction pattern selected from the group consisting of 17.192±0.2°, 19.778±0.2°, 22.799±0.2°, 23.590±0.2° and 27.416±0.2°.

In another embodiment, polymorph V has characteristic peaks in X-ray powder diffraction pattern as essentially shown in FIG. 5a.

In another embodiment, polymorph V has a maximum peak of 130-142.3° C. in differential scanning calorimetry pattern.

In another embodiment, polymorph V has a differential scanning calorimetry pattern as essentially shown in FIG. 5b.

In another embodiment, in polymorph V, the molar ratio of compound I top-toluenesulfonic acid is 2:1.

In another embodiment, the polymorph is polymorph VI of compound I, wherein polymorph VI has one or more characteristic peaks in X-ray powder diffraction pattern selected from the group consisting of 23.818±0.2°, 24.236±0.2°, 26.382±0.2°, 26.817±0.2°, 24.929±0.2° and 27.101±0.2°.

In another embodiment, polymorph VI further has one or more characteristic peaks in X-ray powder diffraction pattern selected from the group consisting of 11.327±0.2°, 17.997±0.2°, 18.528±0.2° and 21.669±0.2°.

In another embodiment, polymorph VI has characteristic peaks in X-ray powder diffraction pattern as essentially shown in FIG. 6a.

In another embodiment, polymorph VI has a maximum peak of 211.5-213.6° C. in differential scanning calorimetry pattern.

In another embodiment, polymorph VI has a differential scanning calorimetry pattern as essentially shown in FIG. 6b.

In the second aspect, it provides a use of the polymorphs of the first aspect of the present invention in preparation of a pharmaceutical composition for inhibiting phosphokinase (such as raf kinase).

In another embodiment, the pharmaceutical composition is used for treating or preventing cancer.

In the third aspect, a pharmaceutical composition is provided, wherein the composition comprises:
(a) the polymorph of the first aspect of the present invention; and
(b) a pharmaceutically acceptable carrier.

In the fourth aspect, a method for preparing the polymorphs of the first aspect of the present invention is provided, comprising a step of: forming salt of compound I with an acid and crystallizing in an inert solvent, or recrystallizing compound I or pharmaceutically acceptable salts thereof or solvates thereof in an inert solvent, thereby obtaining the polymorphs of the first aspect of the present invention.

In another embodiment, the acid is p-toluenesulfonic acid.

In another embodiment, the method for preparing polymorph I comprises a step of: in an inert solvent, recrystallizing compound I with p-toluenesulfonic acid, thereby obtaining the polymorph I of the present invention.

In another embodiment, the method for preparing polymorph II comprises a step of: in methanol, recrystallizing the polymorph I obtained in the aforesaid step, thereby obtaining the polymorph II of the present invention.

In another embodiment, the method for preparing polymorph III comprises a step of: drying the polymorph II obtained in the aforesaid step for a period, thereby obtaining the polymorph III of the present invention.

In another embodiment, the method for preparing polymorph IV comprises a step of: in ethanol, recrystallizing the polymorph I obtained in the aforesaid step, thereby obtaining the polymorph IV of the present invention.

In another embodiment, the method for preparing polymorph V comprises a step of: drying the polymorph I obtained in the aforesaid step for a period, thereby obtaining the polymorph V of the present invention.

It should be understood that in the present invention, any of the technical features specifically described above and below (such as in the Examples) can be combined with each other, thereby constituting new or preferred technical solutions which will not redundantly be described one by one herein.

DETAILED DESCRIPTION OF INVENTION

Figure 1A:
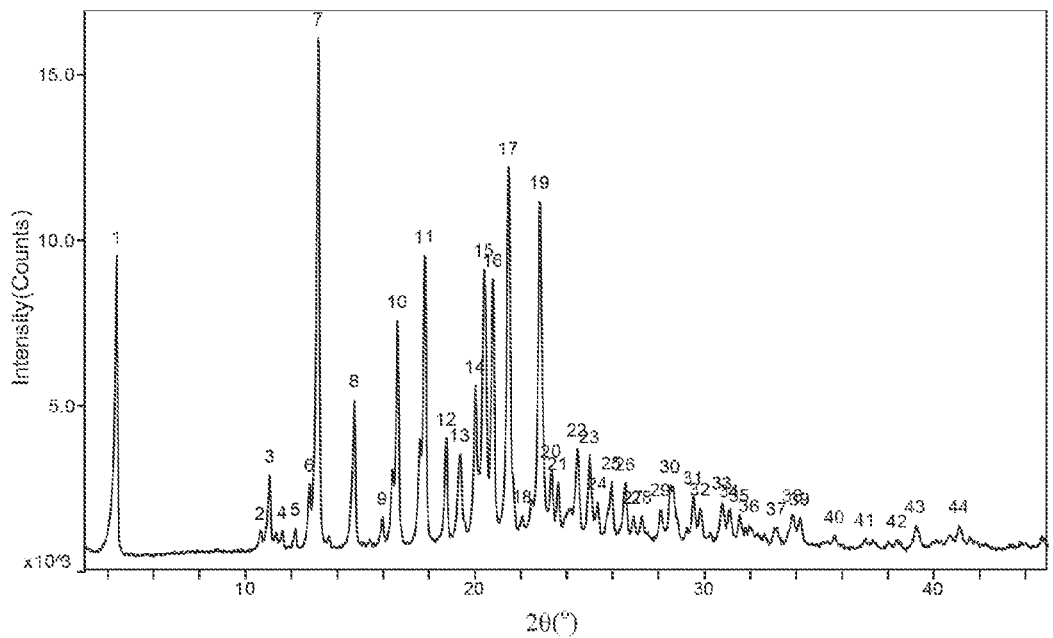
FIG. 1a shows an X-ray powder diffraction pattern of polymorph I of Example 1.

After intensive studies for a long time, the inventors have unexpectedly discovered various polymorphs of compound I or pharmaceutically acceptable salts thereof, or solvates thereof, which are highly pure, very stable, and suitable for preparing pharmaceutical compositions inhibiting phosphokinase (such as raf kinase). Therefore, they are more beneficial for treating diseases such as cancer. Moreover, the polymorphs of the present invention are not prone to floating in the manufacturing process (such as subpackaging) of a drug, easy for collection so that it is easy to avoid wasting and it is helpful to protect the health of operators. Based on this discovery, the inventors have completed the present invention.

As used herein, "Compound of Formula I (or compound I)" refers to 4-(4-{3-[4-chloro-3-(trifluoromethyl)phenyl)-ureido]-phenyl}-2-(N-1',1',1'-trideutero-methyl)pico linamide as shown by Formula I.

p-Toluenesulfonate of 4-(4-{3-[4-chloro-3-(trifluoromethyl)phenyl)-ureido]-phenoxy}-2-(N-1',1',1'-trideutero-methyl)picolinamide The p-toluenesulfonate of 4-(4-{3-[4-chloro-3-(trifluoromethyl)phenyl)-ureido]-phenoxy}-2-(N-1',1',1'-trideutero-methyl)picolinamide of the present invention comprises various forms of the p-toluenesulfonate of compound I.

Preferably, it is the 1/1 p-toluenesulfonate of 4-(4-{3-[4-chloro-3-(trifluoromethyl)phenyl)-ureido]-phenoxy}-2-(N-1',1',1'-trideutero-methyl)pico linamide, which refers to a salt wherein the ratio of compound I and p-toluenesulfonic acid is 1:1; or the 1/2 p-toluenesulfonate of 4-(4-{3-[4-chloro-3-(trifluoromethyl)phenyl)-ureido]-phenoxy}-2-(N-1',1',1'-trideutero-methyl)picolinamide, which refers to a salt wherein the ratio of compound I and p-toluenesulfonic acid is 2:1.

Polymorph

Solid exists in either an amorphous form or a crystal form. In the case of crystal form, the molecules orient in lattice sites of a 3D lattice. When a compound is crystallized from a solution or slurry, it can have various crystalline phases that have different arrangements and/or conformations of the molecules which called as "polymorphism". Different polymorphs of a given substance may be different from each other in one or more physical properties, such as solubility and dissolution rate, true specific gravity, crystal form, accumulation mode, liquidity and/or solid state stability, and so on.

Crystallization

The production-scale crystallization can be achieved by operating a solution so as to exceed the solubility limit of a compound interested. This can be accomplished through a variety of methods, for example, dissolving a compound at a relatively high temperature, and then cooling the solution below a saturation limit, or reducing the liquid volume by boiling, atmospheric evaporation, vacuum drying or some other methods, or reducing the solubility of the interested compound by adding antisolvent or solvents with low solubility of the compound, or a mixture of such solvents. An alternative method is to reduce the solubility by adjusting the pH value. See Crystallization, Third Edition, J W Mullens, Butterworth-Heineman Ltd., 1993, ISBN 0750611294 for a detailed description of crystallization.

If formation of a salt and its crystallization are desired to occur simultaneously, and the solubility of salt is lower than the raw material in the reaction medium, then the salt can be crystallized directly by adding an appropriate acid or base. Similarly, in a medium in which the solubility of the desired final form is lower than that of reactant, the final product can directly crystallize when the synthetic reaction is completed.

Optimization of crystallization may include adding the crystal desired as a seed crystal in the crystallization medium. In addition, many crystallization methods use a combination of the above strategies. One way comprises: dissolving the interested compound in a solvent, then adding an antisolvent in an appropriate volume through a controlled mode, in order to make the system just below the saturation level. At this moment, the desired crystal seed may be added (the integrity of the seed is kept), then crystallization is achieved by cooling the system.

As used herein, the term "room temperature" generally refers to 4-30° C., preferably, 20±5° C.

Polymorph of the Present Invention

As used herein, the term "polymorphs of the present invention" comprises polymorphs of compound I or pharmaceutically acceptable salts thereof (such as the p-toluenesulfonate), or solvates thereof, and further comprises various polymorphs of a certain p-toluenesulfonate or solvates thereof.

The preferable polymorphs of the present invention include but are not limited to:

polymorph VI of compound I;

polymorph I or polymorph III of the 1/1 p-toluenesulfonate of compound I;

polymorph II of methanol solvate of the 1/1 p-toluenesulfonate of compound I or polymorph IV of ethanol solvate of the 1/1 p-toluenesulfonate of compound I; wherein, in polymorph II, the molar ratio of compound I, p-toluenesulfonic acid and methanol is 1:1:1; and in polymorph IV, the molar ratio of compound I, p-toluenesulfonic acid and ethanol is 1:1:1; and polymorph V of the 1/2 p-toluenesulfonate of compound I.

Identification and Property of Polymorph

After preparing polymorphs of the p-toluenesulfonate of compound I, the property thereof is studied using various methods and instruments.

X-Ray Powder Diffraction

The method of X-ray powder diffraction determining crystal form is known in the field. For example, the pattern is obtained using copper radiation on X-ray powder diffractometer of Rigaku D/max 2550VB/PC, at a scanning rate of 2° per minute.

The polymorphs of the p-toluenesulfonate of compound I have a specific crystal form and specific characteristic peaks in X-ray powder diffraction pattern. The preferred embodiments include:

(1) Polymorph I

Polymorph I has one or more characteristic peaks in X-ray powder diffraction pattern selected from the group consisting of 13.182±0.2°, 21.472±0.2° and 22.833±0.2°. In another embodiment, polymorph I further has one or more characteristic peaks in X-ray powder diffraction pattern selected from the group consisting of 4.397±0.2°, 16.636±0.2°, 17.821±0.2°, 20.407±0.2° and 20.782±0.2°. In another embodiment, polymorph I has characteristic peaks in X-ray powder diffraction pattern as essentially shown in FIG. 1a.

(2) Polymorph II

Polymorph II has one or more characteristic peaks in X-ray powder diffraction pattern selected from the group consisting of 21.014±0.2°, 18.333±0.2° and 25.301±0.2°. In another embodiment, polymorph II further has one or more characteristic peaks in X-ray powder diffraction pattern selected from the group consisting of 8.405±0.2°, 15.906±0.2°, 19.477±0.2° and 24.744±0.2°. In another embodiment, polymorph II has characteristic peaks in X-ray powder diffraction pattern as essentially shown in FIG. 2a.

(3) Polymorph III

Polymorph III has 1 or 2 characteristic peaks in X-ray powder diffraction pattern selected from the group consisting of 19.858±0.2° and 25.896±0.2°. In another embodiment, polymorph III further has one or more characteristic peaks in X-ray powder diffraction pattern selected from the group consisting of 17.726±0.2°, 19.325±0.2° and 21.575±0.2°. In another embodiment, polymorph III has characteristic peaks in X-ray powder diffraction pattern as essentially shown in FIG. 3a.

(4) Polymorph IV

Polymorph IV has one or more characteristic peaks in X-ray powder diffraction pattern selected from the group consisting of 20.961±0.2° and 18.277±0.2°. In another embodiment, polymorph IV further has one or more characteristic peaks in X-ray powder diffraction pattern selected from the group consisting of 9.273±0.2°, 15.812±0.2°, 24.674±0.2°, 25.246±0.2° and 27.552±0.2°. In another embodiment, polymorph IV has characteristic peaks in X-ray powder diffraction pattern as essentially shown in FIG. 4a.

(5) Polymorph V

Polymorph V has one or more characteristic peaks in X-ray powder diffraction pattern selected from the group consisting of 13.423±0.2°, 13.974±0.2°, 20.467±0.2°, 20.705±0.2°, 24.929±0.2° and 27.101±0.2°. In another embodiment, polymorph V further has one or more characteristic peaks in X-ray powder diffraction pattern selected from the group consisting of 17.192±0.2°, 19.778±0.2°, 22.799±0.2°, 23.590±0.2° and 27.416±0.2°. In another embodiment, polymorph V has characteristic peaks in X-ray powder diffraction pattern as essentially shown in FIG. 5a.

(6) Polymorph VI

Polymorph VI has one or more characteristic peaks in X-ray powder diffraction pattern selected from the group consisting of 23.818±0.2°, 24.236±0.2°, 26.382±0.2°, 26.817±0.2°, 24.929±0.2° and 27.101±0.2°. In another embodiment, polymorph VI further has one or more characteristic peaks in X-ray powder diffraction pattern selected from the group consisting of 11.327±0.2°, 17.997±0.2°, 18.528±0.2° and 21.669±0.2°. In another embodiment, polymorph VI has characteristic peaks in X-ray powder diffraction pattern as essentially shown in FIG. 6a.

Differential Scanning Calorimetry

Differential scanning calorimetry or DSC refers to a thermoanalytical technique in which the difference in the amount of energy required to increase the temperature of a sample and reference is measured as a function of temperature. Position, shape and number of peaks in DSC pattern are relevant to the properties of substance, so they can be used to identify a substance qualitatively. Generally, this method is use to detect phase transition temperature, glass transition temperature, reaction calorimetry and other parameters of a substance.

The method of DSC is known in the art. For example, differential scanning calorimeter of NETZSCH DSC 204 F1 can be used, at a heating rate of 10 degrees per minute, from 25° C. to 250° C., to obtain a DSC pattern of a crystal form.

The polymorphs of the p-toluenesulfonate of compound I have specific characteristic peaks in Differential Scanning calorimetry (DSC) pattern. Preferably, they are shown as follows:

(1) Polymorph I

Polymorph I has a maximum peak of 231.5-237.7° C. in DSC pattern. In another embodiment, polymorph I has a DSC pattern as essentially shown in FIG. 1b.

(2) Polymorph II

Polymorph II has maximum peaks of 193.5-197.0° C. and 228.6-236.4° C. in DSC pattern. In another embodiment, polymorph II has a DSC pattern as essentially shown in FIG. 2b.

(3) Polymorph III

Polymorph III has maximum peaks of 193.8-197.2° C. and 231.3-236.9° C. in DSC pattern. In another embodiment, polymorph III has a DSC pattern as essentially shown in FIG. 3b.

(4) Polymorph IV

Polymorph IV has maximum peaks of 190.8-192.5° C. and 230.0-237.4° C. in DSC pattern. In another embodiment, polymorph IV has a DSC pattern as essentially shown in FIG. 4b.

(5) Polymorph V

Polymorph V has a maximum peak of 130-142.3° C. in DSC pattern. In another embodiment, polymorph V has a DSC pattern as essentially shown in FIG. 5b.

(6) Polymorph VI

Polymorph VI has a maximum peak of 211.5-213.6° C. in DSC pattern. In another embodiment, polymorph VI has a DSC pattern as essentially shown in FIG. 6b.

Nuclear magnetic resonance (NMR) may further be used to assistantly determine the crystal structure. The detecting methods and instruments are known in the art, for example, one can use Bruker Avance III plus-400 MHz.

Active Ingredients

As used herein, the term "active ingredients" or "active compound" refers to the polymorphs of the present invention, i.e. polymorphs of compound I or pharmaceutically acceptable salts thereof (such as the p-toluenesulfonate), or solvates thereof.

Pharmaceutical Composition and the Administration Thereof

The polymorphs of the present invention possess outstanding activity of inhibiting phosphokinases, such as raf kinases. Therefore, the polymorphs of the present invention and the pharmaceutical composition comprising polymorphs of the present invention as a main active ingredient can be used for treating, preventing and alleviating diseases mediated by phosphokinases (e.g. raf kinase). Based on the prior art, the compounds of the invention can treat the following diseases: cancer, cardiovascular diseases, obesity, diabetes etc.

The pharmaceutical composition of the invention comprises the polymorph of the present invention in a safe and effective dosage range and pharmaceutically acceptable excipients or carriers.

Wherein, the term "safe and effective dosage" refers to the amount of the compounds (or the polymorphs) which is enough to improve the patient's condition without any serious side effect. Generally, the pharmaceutical composition contains 1-2000 mg polymorphs of the invention per dose, preferably, 10-200 mg polymorphs of the invention per dose. Preferably, "per dose" means one capsule or tablet.

"Pharmaceutically acceptable carrier" means one or more compatible solid or liquid fillers or gel materials, which are suitable for human, and must have sufficient purity and sufficiently low toxicity. "Compatibility" herein means that the components of the compositions can be blended with the compounds of the invention or with each other, and would not significantly reduce the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the polymorphs or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active ingredients are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain a opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active ingredients, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active ingredients, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Polymorphs of the present invention can be administrated alone, or in combination with any other pharmaceutically acceptable compounds.

When the pharmaceutical compositions are used, a safe and effective amount of polymorph of the present invention is applied to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The main advantages of the present invention are:

1. a series of novel polymorphs of 4-(4-{3-[4-chloro-3-(trifluoromethyl)phenyl)-ureido]-phenoxy}-2-(N-1',1',1'-trideutero-methyl)picolinamide or salts thereof, or solvates thereof are provided, including polymorphs I to VI;

2. a use of various polymorphs in preparing a pharmaceutical composition useful for inhibiting phosphokinase (such as raf kinase) is provided.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Example 1: Polymorph I of the 1/1 p-toluenesulfonate of 4-(4-{3-[4-chloro-3-(trifluoromethyl)phenyl)-ureido]-phenoxy}-2-(N-1',1',1'-trideuteromethyl)picolinamide 50 g of methyl 4-chloro-2-picolinate was dissolved in 250 mL of tetrahydrofuran in a three-necked flask, then 31 g of deuterated methylamine hydrochloride and 80 g of anhydrous potassium carbonate were added respectively. After the mixture was stirred at 25° C. for 20 hours, 250 mL of water and 100 mL of methyl tert-butyl ether were added. The mixture was stirred and separated, and the aqueous phase was extracted with 100 mL of methyl tert-butyl ether. The organic phases were combined and dried, and the solvent was removed under reduced pressure to give 48 g of pale yellow liquid.

The pale yellow liquid was dissolved in 50 mL of dimethylsulfoxide, then 30 g of 4-aminophenol was added and 31 g of potassium t-butoxide was added in portions. The mixture was heated to 80° C. and stirred for 4 hours. 100 mL of hydrochloric acid was added dropwise, then the mixture was filtered and the filter cake was suspended in 150 mL of acetone. The suspension was stirred at 25° C. for 16 hours and filtered. The filter cake was dissolved in 100 mL of water, and extracted with 200 mL of ethyl acetate twice. The organic phase was dried, and the solvent was removed under reduced pressure to obtain 51 g of light brown solid.

The resultant light brown solid was dissolved in 50 mL of N,N-dimethylformamide. A solution of 4-chloro-3-trifluoromethylphenyl isocyanate (48 g) in ethyl acetate (50 mL) was added dropwise, and the mixture was stirred at 25° C. for 2 hours. Then 130 mL of water was added dropwise, and the mixture was stirred for 1 hour, filtered and dried to give 77 g of pale yellow solid, i.e., 4-(4-{3-[4-chloro-3-(trifluoromethyl)phenyl)-ureido]-phenoxy}-2-(N-1',1',1'-trideutero-methyl)pico linamide.

45 g of pale yellow solid was added into 450 mL of tetrahydrofuran, then 6.6 g of p-toluenesulfonic acid monohydrate was added. The mixture was heated to reflux until the solution was clear. After hot filtration, the filtrate was re-heated to reflux until the solution was clear, then a solution of p-toluenesulfonic acid monohydrate (16.1 g) in tetrahydrofuran (50 mL) at 70° C. was flowed into the above clear solution rapidly. Keep the temperature for 30 minutes, then stop heating and cool to 0° C. The mixture was filtered, and the filter cake was taken out and dried under vacuum for 24 hours at room temperature to constant weight to give 55.2 g of the title compound.

NMR data showed that the molar ratio of compound I and p-toluenesulfonic acid was 1:1.

$^1$H NMR (DMSO-d6, 400 MHz): δ 2.30 (s, 3H), 7.15 (d, J=8.8 Hz, 2H), 7.20 (d, J=8.8 Hz, 2H), 7.23 (dd, J=2.8 Hz, 6 Hz, 1H), 7.52 (d, J=8 Hz, 2H), 7.55 (d, J=2.8 Hz, 1H), 7.63 (d, J=8.8 Hz, 3H), 7.68 (dd, J=2.4 Hz, 9.2 Hz, 1H), 8.03 (br, 1H), 8.14 (d, J=2.4 Hz, 1H), 8.56 (d, J=6 Hz, 1H), 8.91 (br, 1H), 9.17 (br, 1H), 9.36 (br, 1H).

Figure 1B:
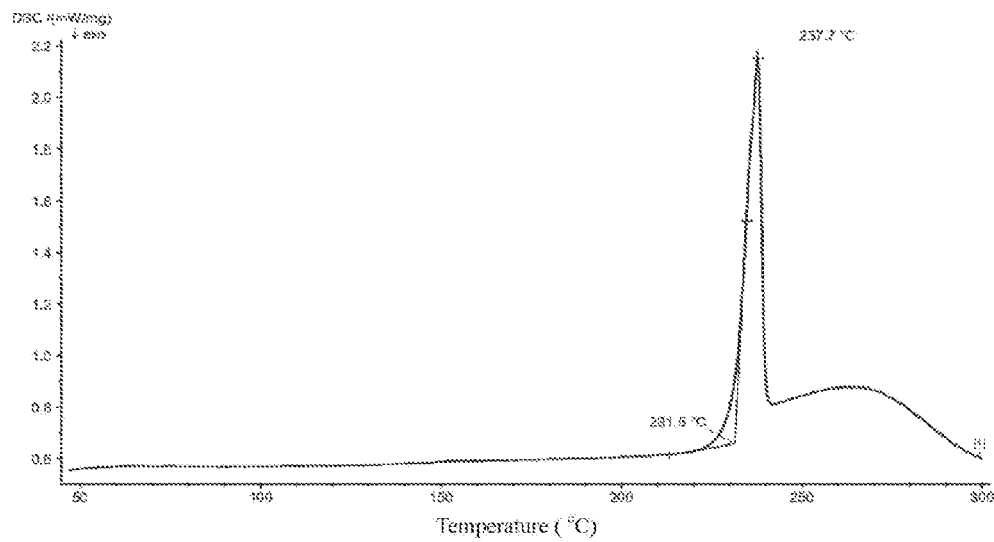
FIG. 1b shows a differential scanning calorimetry pattern of polymorph I of Example 1.
Figure 1C:
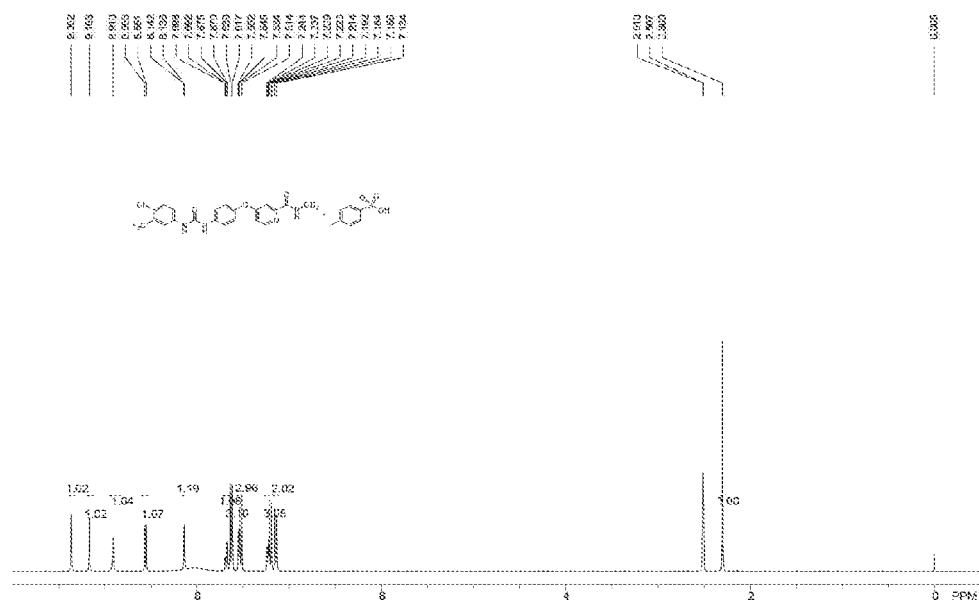
FIG. 1c shows a $^1$H NMR pattern of polymorph I of Example 1.

The X-ray powder diffraction pattern is shown in FIG. 1a, parameters of each peak are shown in Table 1, the differential scanning calorimetry pattern (DSC) is shown in FIG. 1b, and $^1$H NMR is shown in FIG. 1c.

TABLE 1

| Peak No. | 2θ(°) | Height | relative intensity (I %) |
|---|---|---|---|
| 1 | 4.397 | 9535 | 59.02 |
| 2 | 10.643 | 1136 | 7.03 |
| 3 | 11.068 | 2874 | 17.79 |
| 4 | 11.608 | 1178 | 7.29 |
| 5 | 12.193 | 1266 | 7.84 |
| 6 | 12.791 | 2601 | 16.10 |
| 7 | 13.182 | 16155 | 100.00 |
| 8 | 14.759 | 5166 | 31.98 |
| 9 | 15.981 | 1603 | 9.92 |
| 10 | 16.636 | 7569 | 46.85 |
| 11 | 17.821 | 9542 | 59.07 |
| 12 | 18.764 | 4001 | 24.77 |
| 13 | 19.360 | 3516 | 21.76 |
| 14 | 20.030 | 5597 | 34.65 |
| 15 | 20.407 | 9135 | 56.55 |
| 16 | 20.782 | 8830 | 54.66 |
| 17 | 21.472 | 12236 | 75.74 |
| 18 | 22.076 | 1648 | 10.20 |
| 19 | 22.833 | 11201 | 69.33 |
| 20 | 23.345 | 3025 | 18.72 |
| 21 | 23.640 | 2644 | 16.37 |
| 22 | 24.472 | 3676 | 22.75 |
| 23 | 25.005 | 3472 | 21.49 |
| 24 | 25.355 | 2040 | 12.63 |
| 25 | 25.968 | 2673 | 16.55 |
| 26 | 26.578 | 2632 | 16.29 |
| 27 | 26.917 | 1622 | 10.04 |
| 28 | 27.292 | 1631 | 10.10 |
| 29 | 28.101 | 1845 | 11.42 |
| 30 | 28.535 | 2569 | 15.90 |
| 31 | 29.524 | 2219 | 13.74 |
| 32 | 29.837 | 1865 | 11.54 |
| 33 | 30.785 | 2058 | 12.74 |
| 34 | 31.084 | 1812 | 11.22 |
| 35 | 31.538 | 1674 | 10.36 |
| 36 | 31.974 | 1364 | 8.44 |
| 37 | 33.169 | 1275 | 7.89 |
| 38 | 33.863 | 1677 | 10.38 |
| 39 | 34.180 | 1580 | 9.78 |
| 40 | 35.695 | 1035 | 6.41 |
| 41 | 37.021 | 941 | 5.82 |
| 42 | 38.420 | 899 | 5.56 |
| 43 | 39.213 | 1352 | 8.37 |
| 44 | 41.124 | 1354 | 8.38 |

Example 2: Polymorph II of methanol solvate of the 1/1 p-toluenesulfonate of 4-(4-{3-[4-chloro-3-(trifluoromethyl)phenyl)-ureido]-phenoxy}-2-(N-1', 1',1'-trideutero-methyl)pico linamide (The molar ratio of compound I, p-toluenesulfonic acid and methanol is 1:1:1)

10 g of polymorph I prepared in Example 1 was added into 100 g of methanol. The mixture was heated to reflux until the solution was clear, then a solution of p-toluenesulfonic acid monohydrate (6.1 g) in methanol (25 g) was added dropwise. The mixture was cooled to 30° C. naturally after it was clear, and then stirred for 1.5 hours, and filtered. The filter cake was taken out, dried under vacuum at room temperature to constant weight to give 12 g of white solid, which was sampled and characterized through $^1$H NMR, X-ray powder diffraction, DSC, etc., demonstrating that the title compound was obtained.

NMR data showed that the molar ratio of compound I, p-toluenesulfonic acid and methanol was 1:1:1.

$^1$H NMR (DMSO-d6, 400 MHz): δ2.29 (s, 3H), 3.17 (s, 3H), 7.14 (d, J=8 Hz, 2H), 7.20 (d, J=8.2 Hz, 2H), 7.24 (dd, J=2.4 Hz, 6 Hz, 1H), 7.52 (d, J=8 Hz, 2H), 7.57-7.69 (m, 5H), 8.13 (d, J=2 Hz, 1H), 8.38 (br, 1H), 8.56 (d, J=6.4 Hz, 1H), 8.95 (br, 1H), 9.20 (br, 1H), 9.39 (br, 1H).

Figure 2A:
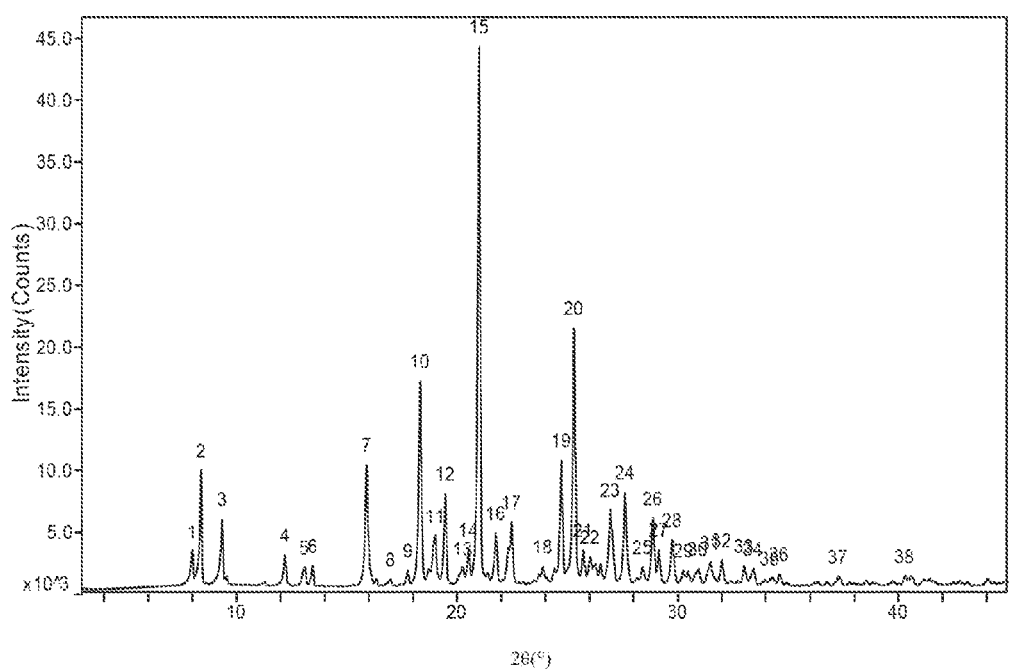
FIG. 2a shows an X-ray powder diffraction pattern of polymorph II of Example 2.
Figure 2B:
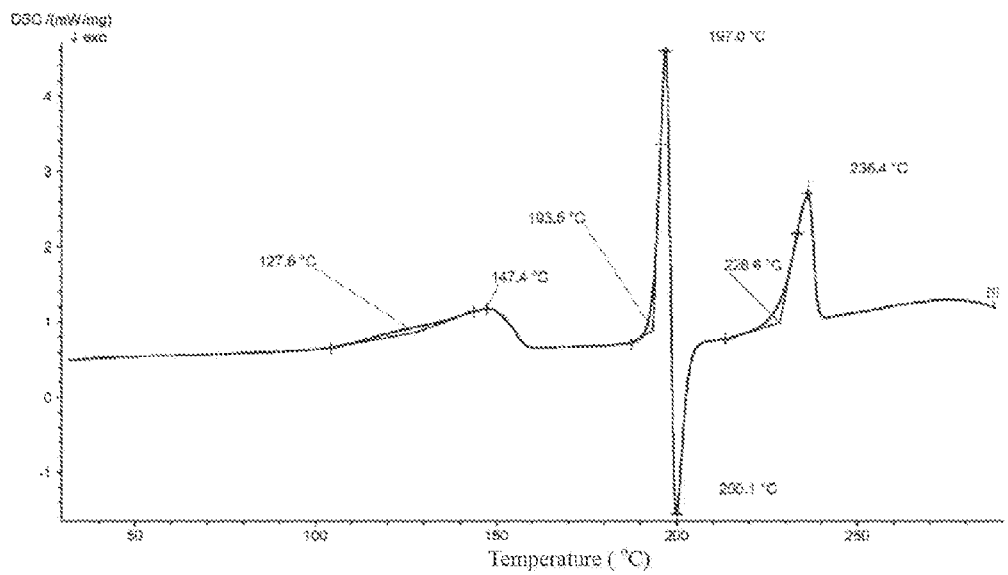
FIG. 2b shows a differential scanning calorimetry pattern of polymorph II of Example 2.
Figure 2C:
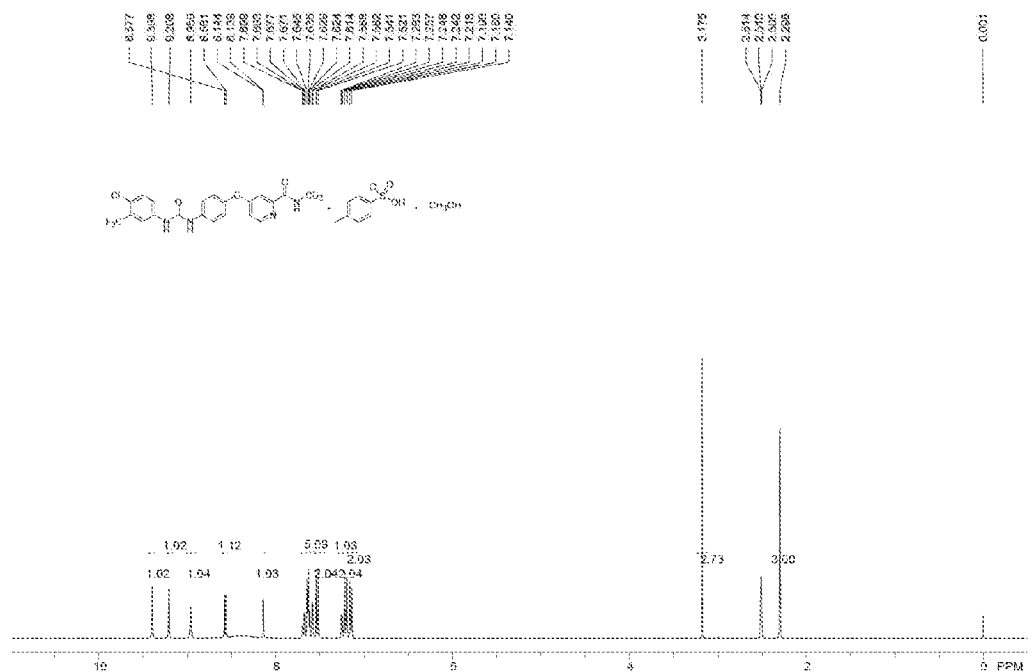
FIG. 2c shows a ¹H NMR pattern of polymorph II of Example 2.

The X-ray powder diffraction pattern is shown in FIG. 2a, parameters of each peak are shown in Table 2, the differential scanning calorimetry pattern (DSC) is shown in FIG. 2b, and $^1$H NMR is shown in FIG. 2c.

TABLE 2

| Peak No. | 2θ(°) | Height | relative intensity (I %) |
|---|---|---|---|
| 1 | 7.996 | 3315 | 7.45 |
| 2 | 8.405 | 9975 | 22.41 |
| 3 | 9.370 | 5972 | 13.42 |
| 4 | 12.214 | 3052 | 6.86 |
| 5 | 13.085 | 2009 | 4.51 |
| 6 | 13.460 | 2179 | 4.90 |
| 7 | 15.906 | 10390 | 23.34 |
| 8 | 16.988 | 1079 | 2.42 |
| 9 | 17.777 | 1790 | 4.02 |
| 10 | 18.333 | 17222 | 38.70 |
| 11 | 19.020 | 4626 | 10.39 |
| 12 | 19.477 | 8049 | 18.08 |
| 13 | 20.281 | 1939 | 4.36 |
| 14 | 20.526 | 3444 | 7.74 |
| 15 | 21.014 | 44507 | 100.00 |
| 16 | 21.768 | 4833 | 10.86 |
| 17 | 22.477 | 5721 | 12.85 |
| 18 | 23.897 | 2109 | 4.74 |
| 19 | 24.744 | 10801 | 24.27 |
| 20 | 25.301 | 21550 | 48.42 |
| 21 | 25.730 | 3443 | 7.74 |
| 22 | 26.034 | 2925 | 6.57 |
| 23 | 26.957 | 6747 | 15.16 |
| 24 | 27.627 | 8140 | 18.29 |
| 25 | 28.416 | 2063 | 4.64 |
| 26 | 28.889 | 6042 | 13.58 |
| 27 | 29.165 | 3503 | 7.87 |
| 28 | 29.760 | 4274 | 9.60 |
| 29 | 30.270 | 1810 | 4.07 |
| 30 | 30.943 | 1966 | 4.42 |
| 31 | 31.494 | 2442 | 5.49 |
| 32 | 32.009 | 2651 | 5.96 |
| 33 | 33.017 | 2159 | 4.85 |
| 34 | 33.430 | 1923 | 4.32 |
| 35 | 34.181 | 1137 | 2.55 |
| 36 | 34.616 | 1512 | 3.40 |
| 37 | 37.281 | 1305 | 2.93 |
| 38 | 40.301 | 1345 | 3.02 |

Example 3: Polymorph III of the 1/1 p-toluenesulfonate of 4-(4-{3-[4-chloro-3-(trifluoromethyl)phenyl}-ureido]-phenoxy}-2-(N-1',1',1'-trideutero-methyl)picolinamide 2 g of polymorph II prepared in example 2 was dried in a vacuum oven at 85° C. for 20 hours to constant weight, which was sampled and determined through $^1$H NMR, X-ray powder diffraction, DSC, etc. The results demonstrated the title compound (1.85 g) was obtained.

NMR data showed that the molar ratio of compound I and p-toluenesulfonic acid was 1:1.

$^1$H NMR (DMSO-d6, 400 MHz): δ2.29 (s, 3H), 3.17 (s, 3H), 7.13 (d, J=8 Hz, 2H), 7.19 (d, J=9.2 Hz, 2H), 7.22 (dd, J=2.4 Hz, 6 Hz, 1H), 7.50-7.53 (m, 3H), 7.60-7.69 (m, 4H), 8.13 (d, J=2.4 Hz, 1H), 8.38 (br, 1H), 8.55 (d, J=5.6 Hz, 1H), 8.90 (br, 1H), 9.15 (br, 1H), 9.35 (br, 1H), 9.63 (br, 1H).

Figure 3A:
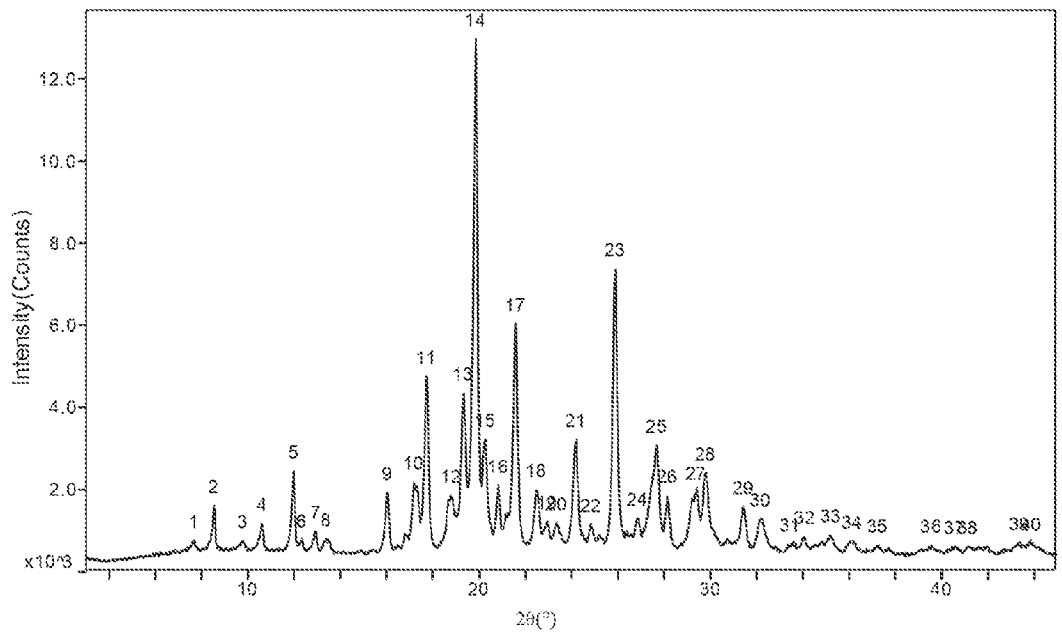
FIG. 3a shows an X-ray powder diffraction pattern of polymorph III of Example 3.
Figure 3B:
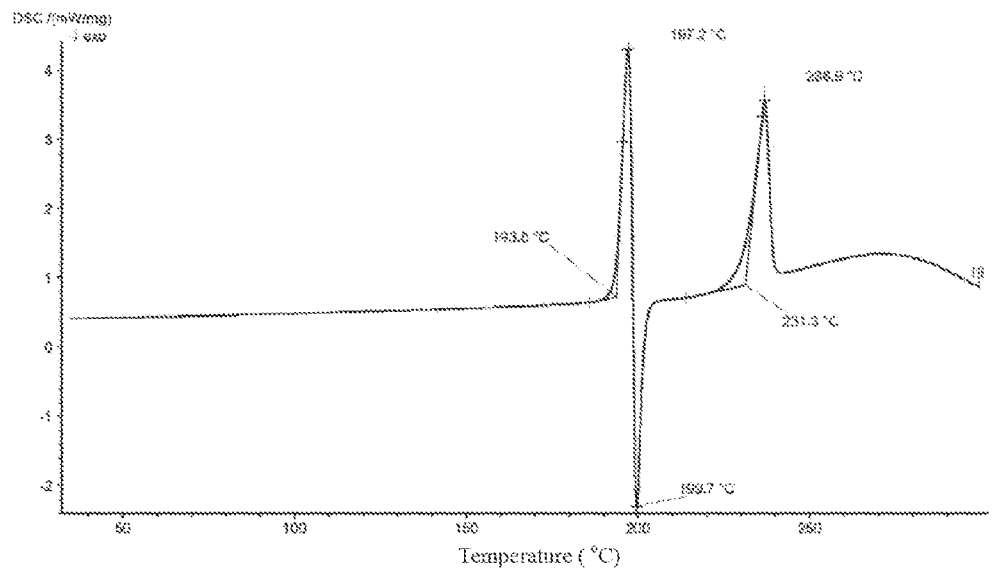
FIG. 3b shows a differential scanning calorimetry pattern of polymorph III of Example 3.
Figure 3C:
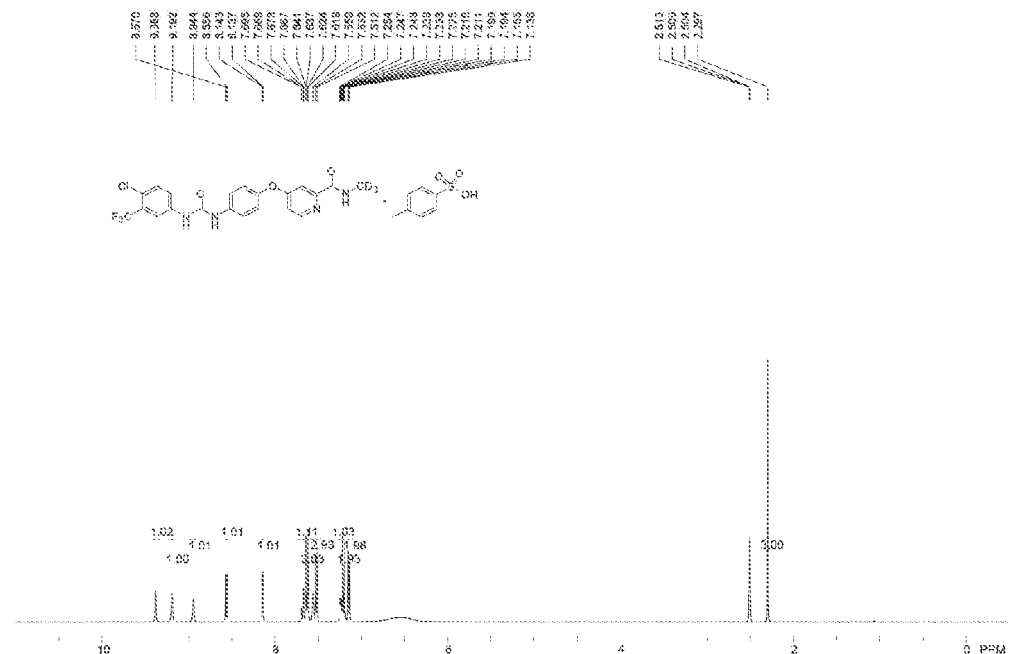
FIG. 3c shows a ¹H NMR pattern of polymorph III of Example 3.

The X-ray powder diffraction pattern is shown in FIG. 3a, parameters of each peak are shown in Table 3, the differential scanning calorimetry diagram (DSC) is shown in FIG. 3b, and $^1$H NMR is shown in FIG. 3c.

TABLE 3

| Peak No. | 2θ(°) | Height | relative intensity (I %) |
|---|---|---|---|
| 1 | 7.676 | 723 | 5.55 |
| 2 | 8.546 | 1575 | 12.09 |
| 3 | 9.773 | 725 | 5.57 |
| 4 | 10.617 | 1144 | 8.78 |
| 5 | 11.982 | 2421 | 18.59 |
| 6 | 12.319 | 740 | 5.68 |
| 7 | 12.926 | 943 | 7.24 |
| 8 | 13.382 | 765 | 5.87 |
| 9 | 16.029 | 1892 | 14.53 |
| 10 | 17.193 | 2155 | 16.55 |
| 11 | 17.726 | 4749 | 36.47 |
| 12 | 18.792 | 1831 | 14.06 |
| 13 | 19.325 | 4336 | 33.29 |
| 14 | 19.858 | 13023 | 100.00 |
| 15 | 20.270 | 3203 | 24.59 |
| 16 | 20.826 | 2077 | 15.95 |
| 17 | 21.575 | 6037 | 46.36 |
| 18 | 22.483 | 1970 | 15.13 |
| 19 | 22.936 | 1186 | 9.11 |
| 20 | 23.370 | 1159 | 8.90 |
| 21 | 24.198 | 3194 | 24.53 |
| 22 | 24.834 | 1112 | 8.54 |
| 23 | 25.896 | 7377 | 56.65 |
| 24 | 26.864 | 1270 | 9.75 |
| 25 | 27.692 | 3058 | 23.48 |
| 26 | 28.149 | 1833 | 14.08 |
| 27 | 29.392 | 1911 | 14.67 |
| 28 | 29.787 | 2386 | 18.32 |
| 29 | 31.443 | 1557 | 11.96 |
| 30 | 32.175 | 1260 | 9.68 |
| 31 | 33.459 | 638 | 4.90 |
| 32 | 34.085 | 817 | 6.27 |
| 33 | 35.212 | 860 | 6.60 |
| 34 | 36.140 | 710 | 5.45 |
| 35 | 37.229 | 608 | 4.67 |
| 36 | 39.557 | 604 | 4.64 |
| 37 | 40.567 | 579 | 4.45 |
| 38 | 41.135 | 582 | 4.47 |
| 39 | 43.382 | 670 | 5.14 |
| 40 | 43.877 | 655 | 5.03 |

Example 4: polymorph IV of ethanol solvate of the 1/1 p-toluenesulfonate of 4-(4-{3-[4-chloro-3-(trifluoromethyl)phenyl)-ureido]-phenoxy}-2-(N-1',1',1'-trideutero-methyl)pico linamide (molar ratio of the compound of formula I, p-toluenesulfonic acid and ethanol is 1:1:1)

5 g of polymorph I prepared in example 1 was suspended in 20 ml of ethanol. The mixture was stirred at room temperature for 16 hours, and filtered. The filter cake out was taken out and dried in vacuo at room temperature for 20 hours to constant weight to give 4.8 g of pale yellow solid, which was sampled and determined through $^1$H NMR, X-ray powder diffraction, DSC, etc., demonstrating that the title compound was obtained.

NMR data showed that the molar ratio of compound I, p-toluenesulfonic acid and ethanol was 1:1:1.

$^1$H NMR (DMSO-d6, 400 MHz): δ1.05 (t, J=6.8 Hz, 3H), 2.29 (s, 3H), 3.44 (q, J=7.2 Hz, 2H), 7.13 (d, J=7.6 Hz, 2H), 7.19 (d, J=8.8 Hz, 2H), 7.22 (dd, J=2.8 Hz, 6 Hz, 1H), 7.51 (d, J=8.4 Hz, 2H), 7.54 (d, J=2.8 Hz, 1H), 7.60-7.69 (m, 4H), 7.97 (br, 1H), 8.13 (d, J=2.4 Hz, 1H), 8.55 (d, J=6 Hz, 1H), 8.92 (br, 1H), 9.16 (br, 1H), 9.36 (br, 1H).

Figure 4A:
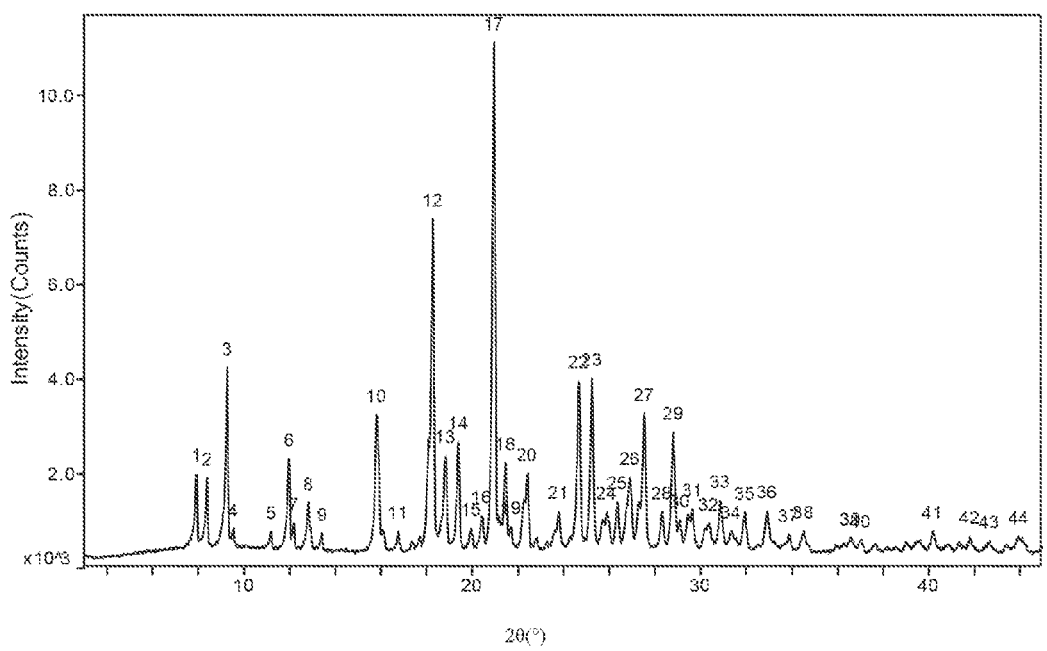
FIG. 4a shows an X-ray powder diffraction pattern of polymorph IV of Example 4.
Figure 4B:
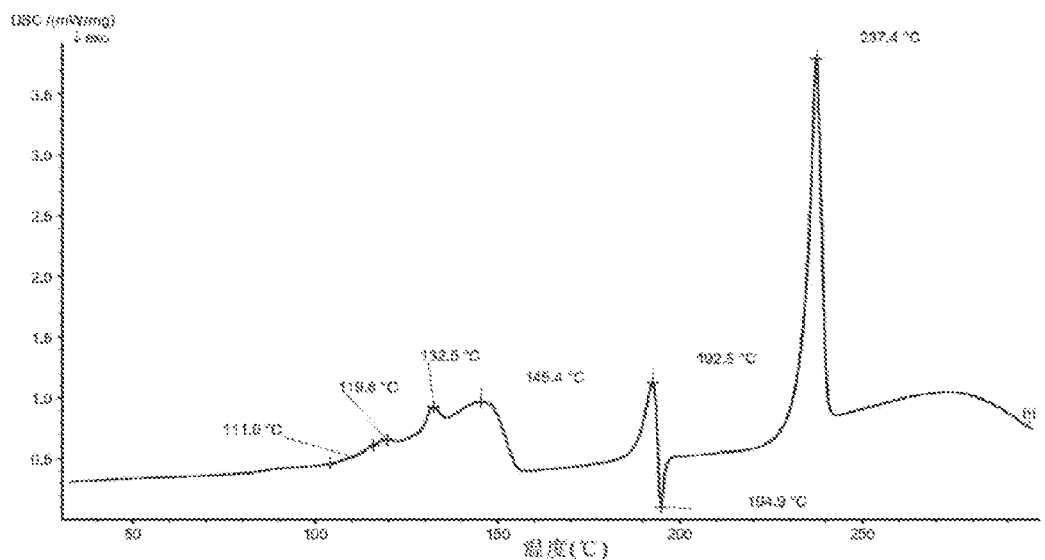
FIG. 4b shows a differential scanning calorimetry pattern of polymorph IV of Example 4.
Figure 4C:
FIG. 4c shows a ¹H NMR pattern of polymorph IV of Example 4.
Figure 4C:
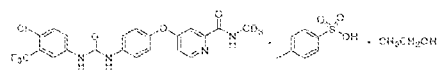
Figure 4C:
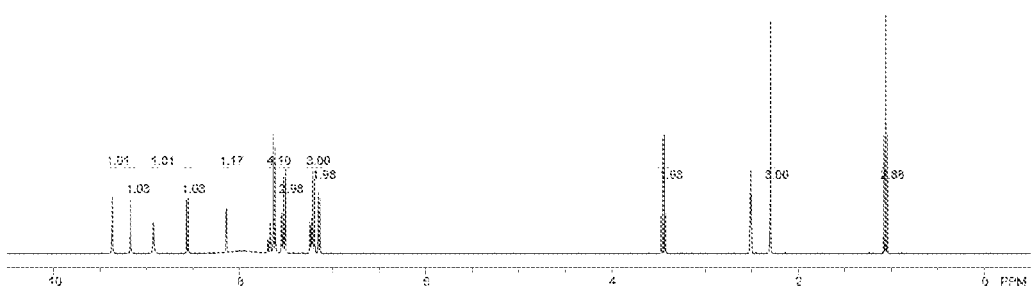

The X-ray powder diffraction pattern is shown in FIG. 4a, parameters of each peak are shown in Table 4, the differential scanning calorimetry pattern (DSC) is shown in FIG. 4b, and ¹H NMR is shown in FIG. 4c.

TABLE 4

| Peak No. | 2θ(°) | Height | relative intensity (I %) |
|---|---|---|---|
| 1 | 7.915 | 1966 | 17.64 |
| 2 | 8.386 | 1884 | 16.90 |
| 3 | 9.273 | 4236 | 38.00 |
| 4 | 9.534 | 786 | 7.05 |
| 5 | 11.186 | 741 | 6.65 |
| 6 | 11.976 | 2299 | 20.63 |
| 7 | 12.178 | 919 | 8.25 |
| 8 | 12.827 | 1362 | 12.22 |
| 9 | 13.417 | 711 | 6.38 |
| 10 | 15.812 | 3239 | 29.06 |
| 11 | 16.759 | 756 | 6.78 |
| 12 | 18.277 | 7399 | 66.38 |
| 13 | 18.832 | 2363 | 21.20 |
| 14 | 19.400 | 2656 | 23.83 |
| 15 | 19.954 | 813 | 7.29 |
| 16 | 20.414 | 1075 | 9.64 |
| 17 | 20.961 | 11146 | 100.00 |
| 18 | 21.456 | 2214 | 19.86 |
| 19 | 21.706 | 851 | 7.64 |
| 20 | 22.422 | 1986 | 17.82 |
| 21 | 23.786 | 1173 | 10.52 |
| 22 | 24.674 | 3954 | 35.47 |
| 23 | 25.246 | 4011 | 35.99 |
| 24 | 25.898 | 1159 | 10.40 |
| 25 | 26.353 | 1382 | 12.40 |
| 26 | 26.922 | 1896 | 17.01 |
| 27 | 27.552 | 3263 | 29.28 |
| 28 | 28.323 | 1168 | 10.48 |
| 29 | 28.818 | 2862 | 25.68 |
| 30 | 29.111 | 996 | 8.94 |
| 31 | 29.646 | 1226 | 11.00 |
| 32 | 30.378 | 920 | 8.25 |
| 33 | 30.872 | 1403 | 12.59 |
| 34 | 31.364 | 752 | 6.75 |
| 35 | 31.954 | 1151 | 10.33 |
| 36 | 32.924 | 1194 | 10.71 |
| 37 | 33.876 | 685 | 6.15 |
| 38 | 34.523 | 753 | 6.76 |
| 39 | 36.578 | 611 | 5.48 |
| 40 | 37.030 | 566 | 5.08 |
| 41 | 40.171 | 754 | 6.76 |
| 42 | 41.809 | 644 | 5.78 |
| 43 | 42.673 | 551 | 4.94 |
| 44 | 43.957 | 630 | 5.65 |

Example 5: Polymorph V of the 1/2 p-toluenesulfonate of 4-(4-{3-[4-chloro-3-(trifluoromethyl)phenyl)-ureido]-phenoxy}-2-(N-1',1',1'-trideuteromethyl)pico linamide 3 g of polymorph I prepared in example 1 was suspended in 50 ml of water. The mixture was stirred at room temperature for 24 hours, and filtered. The filter cake was taken out and dried in vacuo at room temperature for 48 hours, which was sampled and determined through ¹H NMR, X-ray powder diffraction, DSC, etc., demonstrating that 1.2 g of title compound was obtained.

NMR data showed that the molar ratio of compound I and p-toluenesulfonic acid was 2:1.

¹H NMR (DMSO-d6, 400 MHz): δ2.29 (s, 1.5H), 7.13 (d, J=8 Hz, 1H), 7.17-7.20 (m, 3H), 7.46 (d, J=2.4 Hz, 1H), 7.51 (d, J=8 Hz, 2H), 7.60-7.66 (m, 4H), 8.13 (d, J=2.4 Hz, 1H), 8.53 (d, J=6 Hz, 1H), 8.84 (br, 1H), 9.09 (br, 1H), 9.29 (br, 1H).

Figure 5A:
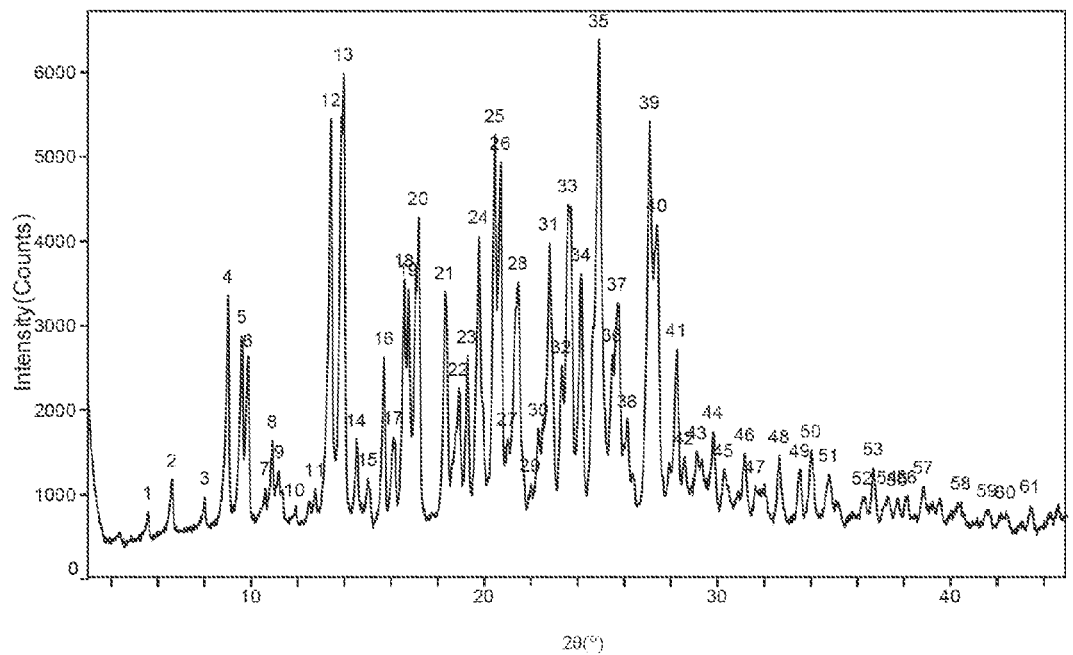
FIG. 5a shows an X-ray powder diffraction pattern of polymorph V of Example 5.
Figure 5B:
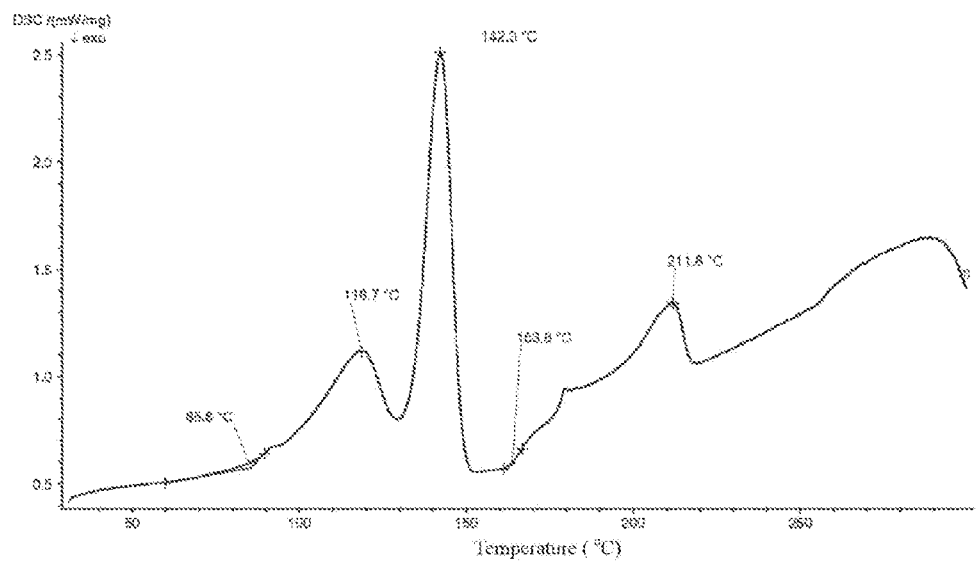
FIG. 5b shows a differential scanning calorimetry pattern of polymorph V of Example 5.
Figure 5C:
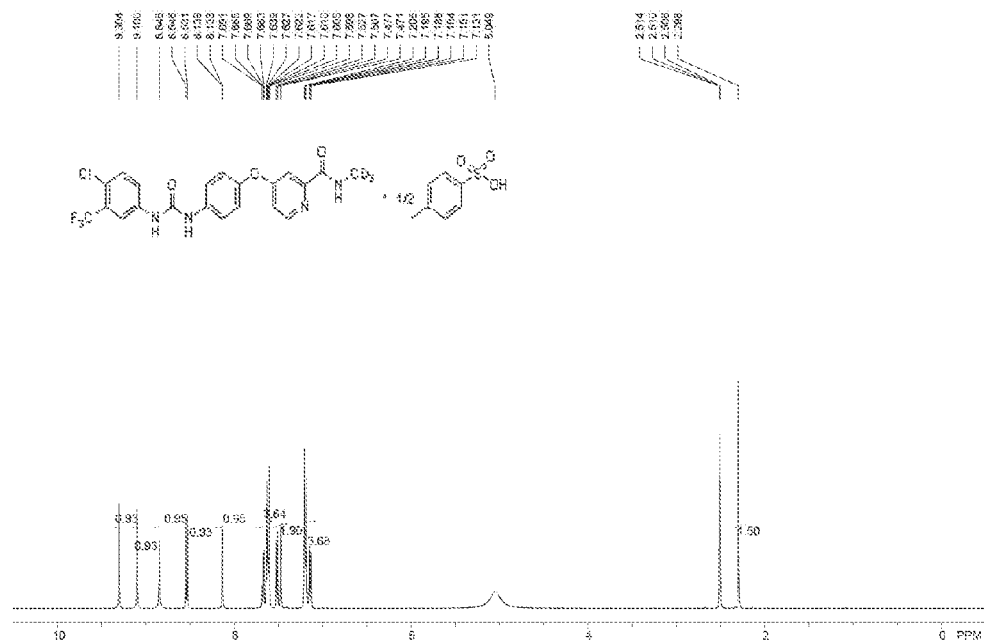
FIG. 5c shows a ¹H NMR pattern of polymorph V of Example 5.

The X-ray powder diffraction pattern is shown in FIG. 5a, parameters of each peak are shown in Table 5, the differential scanning calorimetry diagram (DSC) is shown in FIG. 5b, and ¹H NMR is shown in FIG. 5c.

TABLE 5

| Peak No. | 2θ(°) | Height | relative intensity (I %) |
|---|---|---|---|
| 1 | 5.570 | 779 | 12.17 |
| 2 | 6.611 | 1161 | 18.13 |
| 3 | 8.010 | 959 | 14.98 |
| 4 | 9.017 | 3356 | 52.42 |
| 5 | 9.595 | 2872 | 44.86 |
| 6 | 9.869 | 2591 | 40.47 |
| 7 | 10.601 | 1063 | 16.60 |
| 8 | 10.914 | 1625 | 25.38 |
| 9 | 11.207 | 1266 | 19.78 |
| 10 | 11.891 | 814 | 12.71 |
| 11 | 12.749 | 1053 | 16.45 |
| 12 | 13.423 | 5460 | 85.29 |
| 13 | 13.974 | 6003 | 93.77 |
| 14 | 14.530 | 1645 | 25.70 |
| 15 | 15.019 | 1178 | 18.40 |
| 16 | 15.709 | 2621 | 40.94 |
| 17 | 16.108 | 1667 | 26.04 |
| 18 | 16.578 | 3549 | 55.44 |
| 19 | 16.757 | 3439 | 53.72 |
| 20 | 17.192 | 4282 | 66.89 |
| 21 | 18.320 | 3397 | 53.06 |
| 22 | 18.911 | 2251 | 35.16 |
| 23 | 19.283 | 2641 | 41.25 |
| 24 | 19.778 | 4064 | 63.48 |
| 25 | 20.467 | 5269 | 82.30 |
| 26 | 20.705 | 4945 | 77.24 |
| 27 | 21.003 | 1656 | 25.87 |
| 28 | 21.455 | 3511 | 54.84 |
| 29 | 22.000 | 1110 | 17.34 |
| 30 | 22.341 | 1770 | 27.65 |
| 31 | 22.799 | 3980 | 62.17 |
| 32 | 23.314 | 2515 | 39.28 |
| 33 | 23.590 | 4436 | 69.29 |
| 34 | 24.159 | 3616 | 56.48 |
| 35 | 24.929 | 6402 | 100.00 |
| 36 | 25.503 | 2651 | 41.41 |
| 37 | 25.721 | 3267 | 51.03 |
| 38 | 26.149 | 1873 | 29.26 |
| 39 | 27.101 | 5429 | 84.80 |
| 40 | 27.416 | 4202 | 65.64 |
| 41 | 28.265 | 2716 | 42.42 |
| 42 | 28.599 | 1432 | 22.37 |
| 43 | 29.133 | 1490 | 23.27 |
| 44 | 29.826 | 1737 | 27.13 |
| 45 | 30.282 | 1282 | 20.02 |
| 46 | 31.185 | 1473 | 23.01 |
| 47 | 31.625 | 1087 | 16.98 |
| 48 | 32.666 | 1453 | 22.70 |
| 49 | 33.551 | 1282 | 20.02 |
| 50 | 34.030 | 1512 | 23.62 |
| 51 | 34.781 | 1225 | 19.13 |
| 52 | 36.242 | 959 | 14.98 |
| 53 | 36.693 | 1297 | 20.26 |
| 54 | 37.308 | 965 | 15.07 |
| 55 | 37.722 | 933 | 14.57 |
| 56 | 38.155 | 974 | 15.21 |
| 57 | 38.845 | 1077 | 16.82 |
| 58 | 40.461 | 898 | 14.03 |
| 59 | 41.568 | 802 | 12.53 |
| 60 | 42.383 | 780 | 12.18 |
| 61 | 43.427 | 850 | 13.28 |

Example 6: polymorph VI of 4-(4-{3-[4-chloro-3-(trifluoromethyl)phenyl)-ureido]-phenoxy}-2-(N-1',1',1'-trideutero-methyl)picolinamide 50 g of methyl 4-chloro-2-picolinate was dissolved in 250 mL of tetrahydrofuran in three-necked flask, then 31 g of deuterated methylamine hydrochloride and 80 g of anhydrous potassium carbonate were added respectively. After the mixture was stirred at 25° C. for 20 hours, 250 mL of water and 100 mL of methyl tert-butyl ether were added, The mixture was stirred and separated, and the aqueous phase was extracted with 100 mL of methyl tert-butyl ether. The organic phases were combined and dried, the solvent was removed under reduced pressure to give 48 g of pale yellow liquid.

The pale yellow liquid was dissolved in 50 mL of dimethylsulfoxide, 30 g of 4-aminophenol was added and 31 g of potassium t-butoxide was added in portions. The mixture was heated to 80° C. and stirred for 4 hours. 100 mL of hydrochloric acid was added dropwise, then the mixture was filtered and the filter cake was suspended in 150 mL of acetone. The suspension was stirred at 25° C. for 16 hours, and filtered. The filter cake was dissolved in 100 mL of water, and extracted with 200 mL of ethyl acetate twice. The organic phase was dried, and the solvent was removed under reduced pressure to obtain 51 g of light brown solid.

The resultant light brown solid was dissolved in 50 mL of N,N-dimethylformamide. A solution of 4-chloro-3-trifluoromethylphenyl isocyanate (48 g) in ethyl acetate (50 mL) was added dropwise, and the mixture was stirred at 25° C. for 2 hours. Then 130 mL of water was added dropwise, and the mixture was stirred for 1 hour, filtered and dried in vacuo at 25° C. for 24 hours to give a pale yellow solid, which was sampled and determined through $^1$H NMR, X-ray powder diffraction, DSC, etc., demonstrating that the title compound (77 g) was obtained.

$^1$H NMR (DMSO-d6, 400 MHz): δ7.15 (dd, J=2.8 Hz, 5.6 Hz, 1H), 7.17-7.19 (m, 2H), 7.40 (d, J=2.4 Hz, 1H), 7.59-7.69 (m, 4H), 8.13 (d, J=2.4 Hz, 1H), 8.51 (d, J=6 Hz, 1H), 8.75 (br, 1H), 8.90 (br, 1H), 9.22 (br, 1H).

Figure 6A:
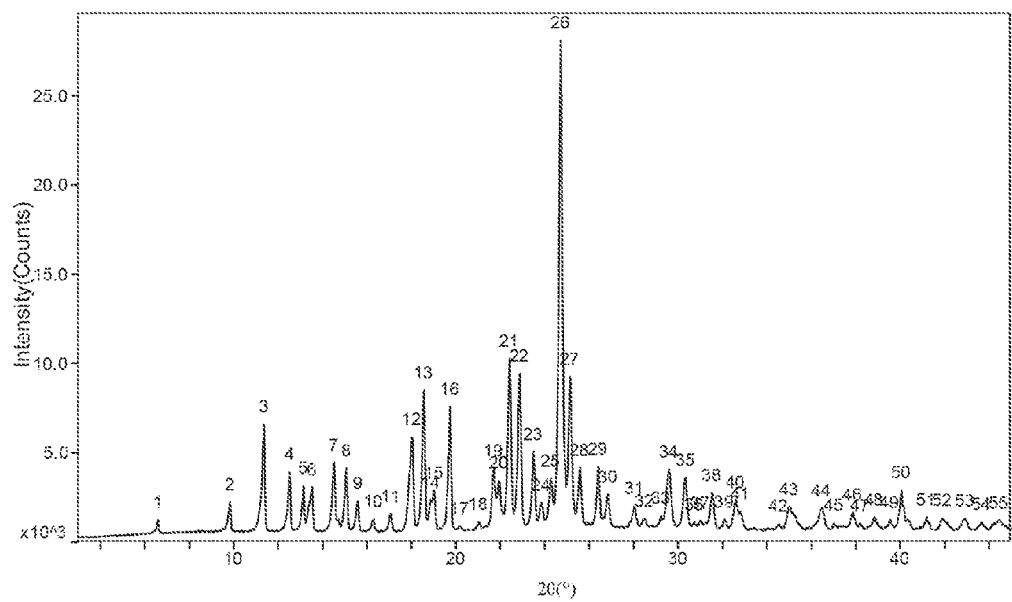
FIG. 6a shows an X-ray powder diffraction pattern of polymorph VI of Example 6.
Figure 6B:
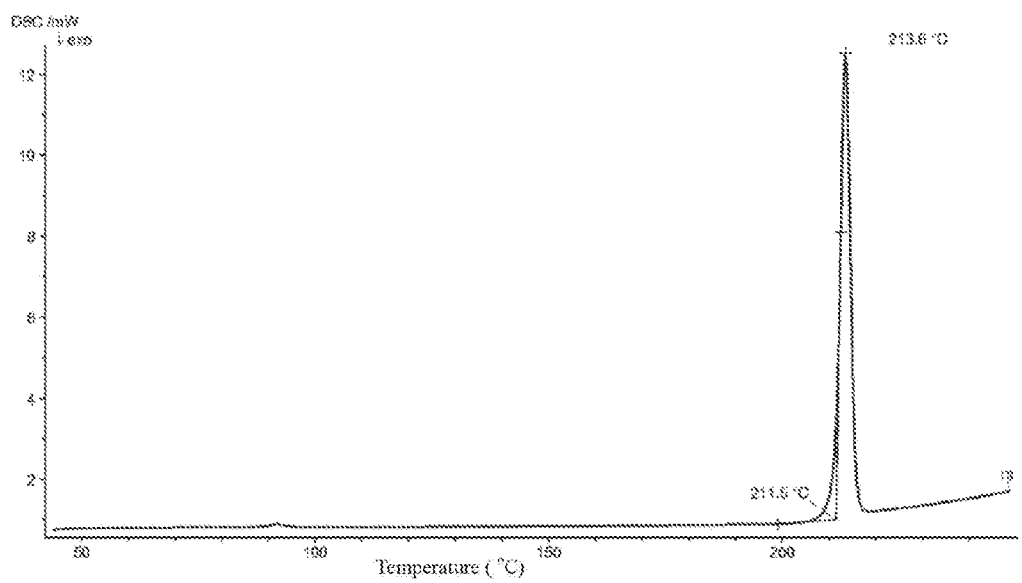
FIG. 6b shows a differential scanning calorimetry pattern of polymorph VI of Example 6.
Figure 6C:
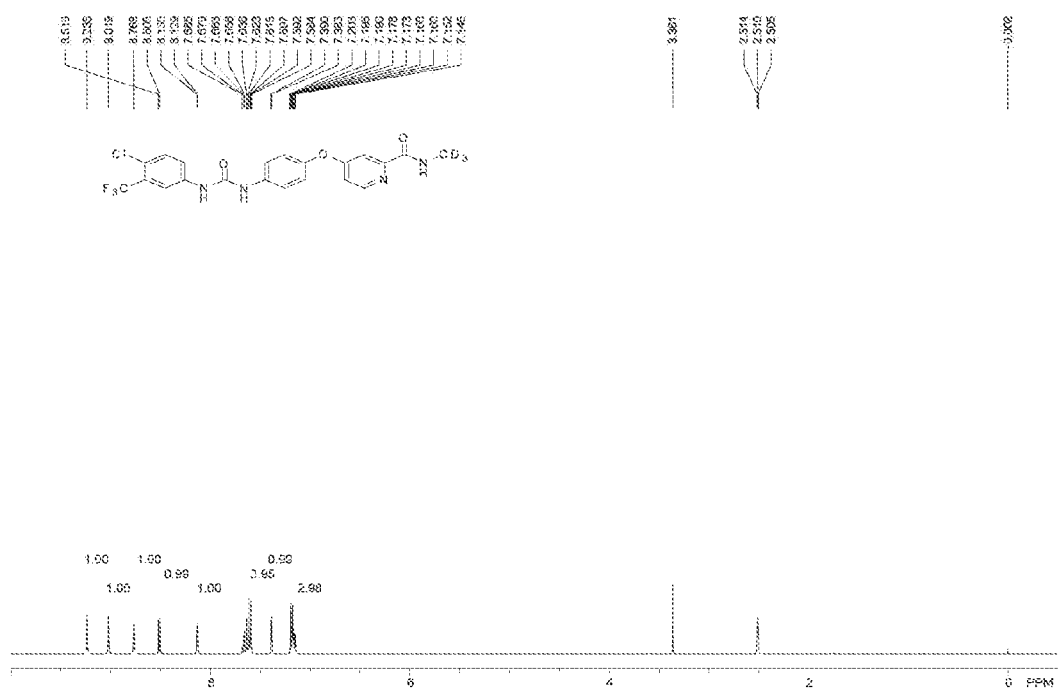
FIG. 6c shows a ¹H NMR pattern of polymorph VI of Example 6.

The X-ray powder diffraction pattern is shown in FIG. 6a, parameters of each peak are shown in Table 6, the differential scanning calorimetry diagram (DSC) is shown in FIG. 6b, and $^1$H NMR is shown in FIG. 6c.

TABLE 6

| Peak No. | 2θ(°) | Height | relative intensity (I %) |
|---|---|---|---|
| 1 | 6.549 | 1062 | 2.18 |
| 2 | 9.806 | 2156 | 4.42 |
| 3 | 11.327 | 5816 | 11.94 |
| 4 | 12.490 | 17961 | 36.86 |
| 5 | 13.105 | 2458 | 5.04 |
| 6 | 13.496 | 3135 | 6.43 |
| 7 | 14.484 | 5096 | 10.46 |
| 8 | 15.037 | 4170 | 8.56 |
| 9 | 15.551 | 3156 | 6.48 |
| 10 | 16.257 | 1228 | 2.52 |
| 11 | 17.033 | 2348 | 4.82 |
| 12 | 17.997 | 4940 | 10.14 |
| 13 | 18.528 | 5423 | 11.13 |
| 14 | 18.985 | 4093 | 8.40 |
| 15 | 19.711 | 5440 | 11.16 |
| 16 | 21.669 | 3610 | 7.41 |
| 17 | 21.925 | 7892 | 16.20 |
| 18 | 22.379 | 14496 | 29.75 |
| 19 | 22.834 | 27515 | 56.47 |
| 20 | 23.465 | 4326 | 8.88 |
| 21 | 23.818 | 2862 | 5.87 |
| 22 | 24.236 | 5232 | 10.74 |
| 23 | 24.686 | 48724 | 100.00 |
| 24 | 25.105 | 33185 | 68.11 |
| 25 | 25.555 | 7452 | 15.29 |
| 26 | 26.382 | 3451 | 7.08 |
| 27 | 26.817 | 4602 | 9.45 |
| 28 | 28.002 | 1827 | 3.75 |
| 29 | 28.418 | 1641 | 3.37 |
| 30 | 29.561 | 4191 | 8.60 |
| 31 | 30.293 | 3754 | 7.70 |
| 32 | 31.514 | 2316 | 4.75 |

TABLE 6-continued

| Peak No. | 2θ(°) | Height | relative intensity (I %) |
|---|---|---|---|
| 33 | 32.543 | 1872 | 3.84 |
| 34 | 32.779 | 1838 | 3.77 |
| 35 | 34.990 | 2317 | 4.76 |
| 36 | 36.390 | 2058 | 4.22 |
| 37 | 37.849 | 2329 | 4.78 |
| 38 | 38.779 | 1223 | 2.51 |
| 39 | 40.021 | 2093 | 4.30 |
| 40 | 41.149 | 1194 | 2.45 |
| 41 | 41.913 | 1084 | 2.22 |
| 42 | 42.784 | 1718 | 3.53 |

Example 7: Amorphous form of the 1/1 p-toluenesulfonate of 4-(4-{3-[4-chloro-3-(trifluoromethyl)phenyl)-ureido]-phenoxy}-2-(N-1',1',1'-trideuteromethyl)pico linamide 0.5 g of polymorph I prepared in example 1 was suspended in 500 mL of ethanol. The mixture was heated under reflux until it was completely dissolved. The solvent was removed under reduced pressure at 80° C. using rotary evaporation, and the solid was dried in vacuo at 50° C. for 28 hours and milled to give a pale yellow powder, which was sampled and determined through $^1$H NMR, X-ray powder diffraction, DSC, etc., demonstrating that 0.41 g of the title compound was obtained.

NMR data showed that the molar ratio of compound I and p-toluenesulfonic acid was 1:1.

$^1$H NMR (DMSO-d6, 400 MHz): δ2.30 (s, 3H), 7.15 (d, J=8.8 Hz, 2H), 7.20 (d, J=8.8 Hz, 2H), 7.23 (dd, J=2.8 Hz, 6 Hz, 1H), 7.52 (d, J=8 Hz, 2H), 7.55 (d, J=2.8 Hz, 1H), 7.63 (d, J=8.8 Hz, 3H), 7.68 (dd, J=2.4 Hz, 9.2 Hz, 1H), 8.03 (br, 1H), 8.14 (d, J=2.4 Hz, 1H), 8.56 (d, J=6 Hz, 1H), 8.91 (br, 1H), 9.17 (br, 1H), 9.36 (br, 1H).

Figure 7A:
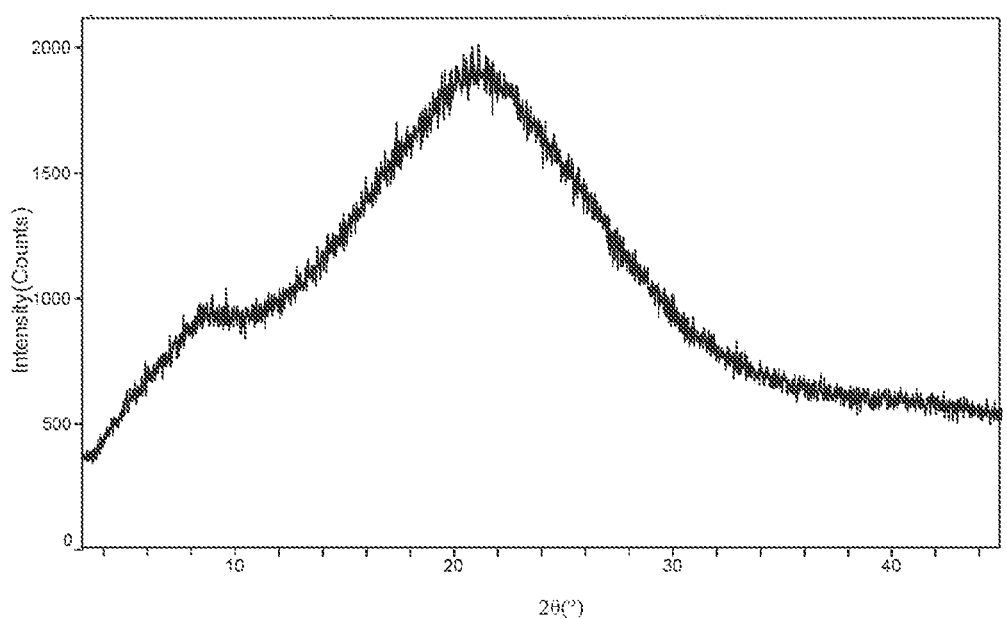
FIG. 7a shows an X-ray powder diffraction pattern of amorphous form of the p-toluenesulfonate of compound I.
Figure 7B:
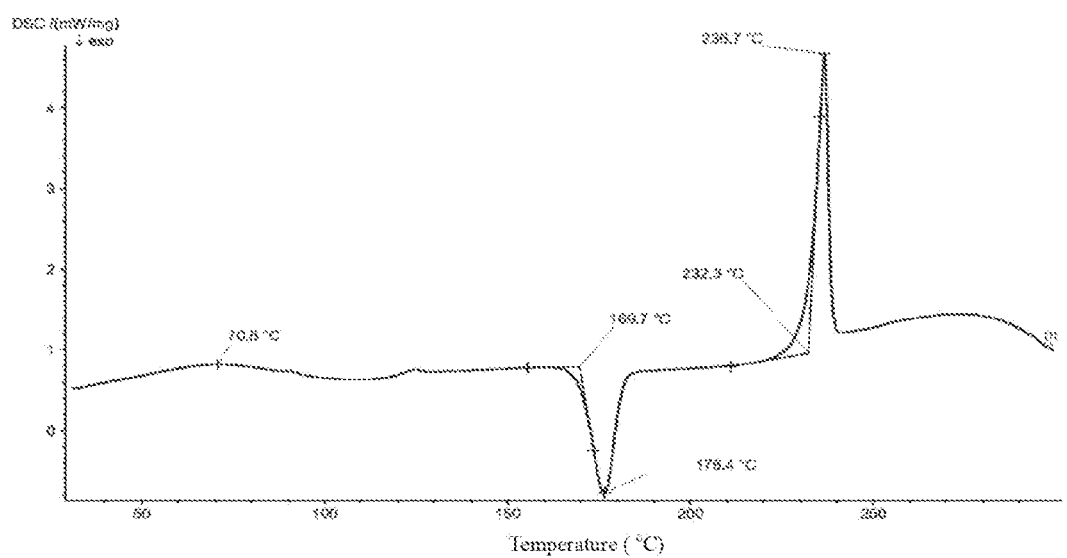
FIG. 7b shows a differential scanning calorimetry pattern of amorphous form of the p-toluenesulfonate of compound I.
Figure 7C:
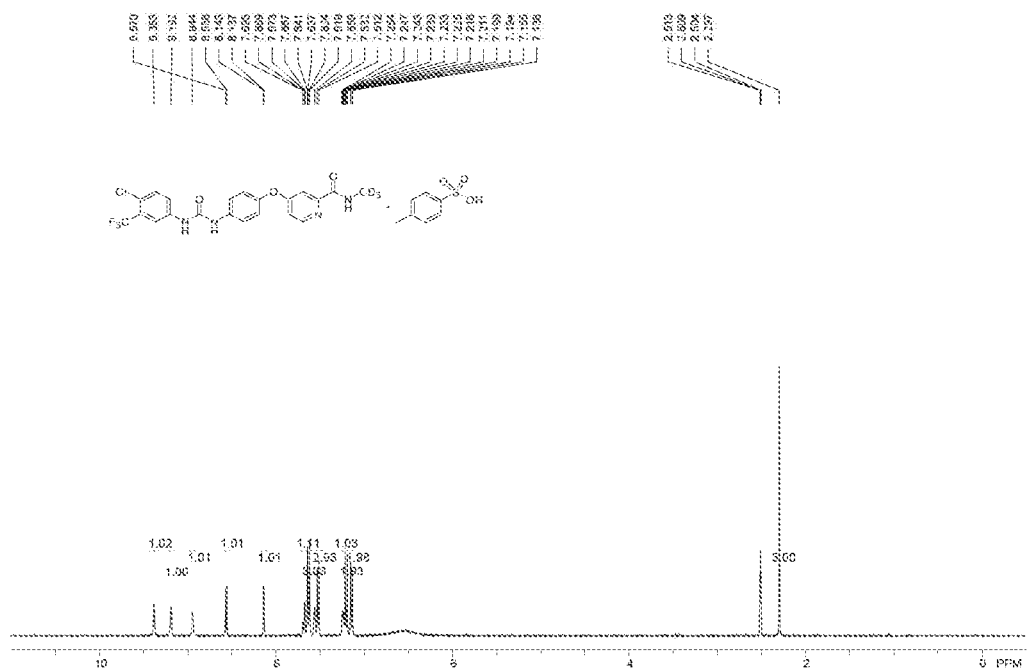
FIG. 7c shows a ¹H NMR pattern of amorphous form of the p-toluenesulfonate of compound I.

The X-ray powder diffraction pattern is shown in FIG. 7a, the differential scanning calorimetry pattern (DSC) is shown in FIG. 7b, and $^1$H NMR is shown in FIG. 7c.

Example 8: Stability of polymorph I of the 1/1 p-toluenesulfonate of 4-(4-{3-[4-chloro-3-(trifluoromethyl)phenyl)-ureido]-phenoxy}-2-(N-1',1',1'-trideutero-methyl)pico linamide After an accelerated stability test (test condition: 40° C., 75% RH) for 1-6 months, the results showed that: crystal form of polymorph I was very stable; compared to polymorph I freshly prepared (0 Months), the purity of polymorph I was almost unchanged, always above 99%.

Example 9: Pharmaceutical Composition

| | |
|---|---|
| Polymorph I of the 1/1 p-toluenesulfonate of 4-(4-{3-[4-chloro-3-(trifluoromethyl)phenyl)-ureido]-phenoxy}-2-(N-1',1',1'-trideutero-methyl)picolinamide (Example 1) | 20 g |
| Starch | 140 g |
| Microcrystalline cellulose | 60 g |

According to the conventional method, the above materials were mixed and encapsulated into ordinary gelatin capsule to give 1,000 capsules.

Example 10: Drug Hygroscopicity Test

The test was performed according to the guiding principles of drug hygroscopic test (Chinese Pharmacopoeia 2010 edition, Appendix XIX J).

1. Take 4 dry glass weighing bottles with a top (The outer diameter was 60 mm and height was 30 mm). On the day before the test, the bottles was placed in a glass dryer (A saturated ammonium sulfate solution was placed in the lower part thereof) in a thermostatic and humidistatic chamber at 25° C.±1° C. (hereinafter, "a humidistatic dryer at 25° C.±1° C."). The weighing bottle and its top were placed separately without the top on the bottle. Cover the glass dryer closely.

2. After each empty weighing bottle together with its top were placed in a humidistatic dryer at 25° C.±1° C. for 24 hours, weigh a set (the weighing bottle+its top) as a unit precisely respectively, recorded as m1. Take a sample appropriately, tile it in a glass weighing bottle weighed at a sample thickness of about 1 mm, and cover the bottle. Precisely weigh the weighing bottle with its top and the sample, recorded as m2. Put 4 kinds of salts of free alkali compound I (ZJCM03) in 4 weighing bottles respectively. Then take off the top of the weighing bottles, and put the bottle and its top in the humidistatic dryer at 25° C.±1° C. for 24 hours.

3. After each sample were placed in a humidistatic dryer at 25° C.±1° C. for 24 hours, cover the weighing bottles with their tops respectively, and precisely weigh each weighing bottle with its top and the sample at this specific moment, recorded as m3.

4. Calculate the weight increase (%) of each sample according to the following equation.

the weight increase (%)=[(m3−m2)/(m2−m1)]×100%

It is defined as no or almost no hygroscopicity when the weight increase (%) is less than 0.2%.

According to the above steps, the hygroscopicity of the polymorphs of the present invention was tested. The results showed that the weight increase (%) of polymorph I=[(39.951−39.951)/(39.951−38.836)]×100%=0. The result showed that polymorph I had no hygroscopicity.

Repeat Example 8 and Example 10 except that polymorphs II, III, IV, V or VI was used instead of polymorph I. The results showed that each polymorph of the present invention was very stable, had no or almost no hygroscopicity.

Therefore, polymorphs of the present invention are very suitable to be used in pharmaceutical compositions. Moreover, the polymorphs of the present invention, which are not prone to floating in the manufacturing process (such as subpackaging) of a drug and are easy for collection so that it is easy to avoid wasting and it is helpful to protect the health of operators.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

What we claim:

1. A method of inhibiting phosphokinase in a subject in need thereof, comprising administering to the subject a pharmaceutical composition comprising an effective amount of a polymorph of a pharmaceutically acceptable p-toluensulfonate salt of compound I,

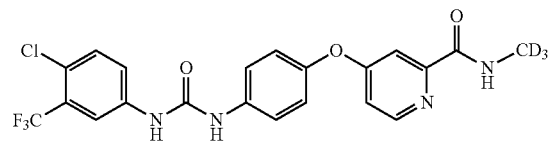

the polymorph being selected from the group consisting of polymorph I, III, and V of the p-toluenesulfonate of compound I, and polymorph IV of ethanol solvate of the p-toluenesulfonate of compound I, wherein:

the polymorph I is polymorph I of the 1/1 p-toluenesulfonate of compound I, and the polymorph I comprises the following characteristic peaks in X-ray powder diffraction pattern:

| Peak No. | 2θ(°) |
| --- | --- |
| 1 | 4.397 |
| 2 | 10.643 |
| 3 | 11.068 |
| 4 | 11.608 |
| 5 | 12.193 |
| 6 | 12.791 |
| 7 | 13.182 |
| 8 | 14.759 |
| 9 | 15.981 |
| 10 | 16.636 |
| 11 | 17.821 |
| 12 | 18.764 |
| 13 | 19.360 |
| 14 | 20.030 |
| 15 | 20.407 |
| 16 | 20.782 |
| 17 | 21.472 |
| 18 | 22.076 |
| 19 | 22.833 |
| 20 | 23.345 |
| 21 | 23.640 |
| 22 | 24.472 |
| 23 | 25.005 |
| 24 | 25.355 |
| 25 | 25.968 |
| 26 | 26.578 |
| 27 | 26.917 |
| 28 | 27.292 |
| 29 | 28.101 |
| 30 | 28.535 |
| 31 | 29.524 |
| 32 | 29.837 |
| 33 | 30.785 |
| 34 | 31.084 |
| 35 | 31.538 |
| 36 | 31.974 |
| 37 | 33.169 |
| 38 | 33.863 |
| 39 | 34.180 |
| 40 | 35.695 |
| 41 | 37.021 |
| 42 | 38.420 |
| 43 | 39.213 |
| 44 | 41.124 | and the polymorph I has a maximum peak of 237.7° C. in differential scanning calorimetry pattern;

the polymorph III is polymorph III of the 1/1 p-toluenesulfonate of compound I, and the polymorph III comprises the following characteristic peaks in X-ray powder diffraction pattern: 19.858±0.2°, 25.896±0.2°, 17.726±0.2°, 19.325±0.2° and 21.575±0.2°;

the polymorph V is polymorph V of the 1/2 p-toluenesulfonate of compound I, and the polymorph V comprises the following characteristic peaks in X-ray powder diffraction pattern: 13.423±0.2°, 13.974±0.2°, 20.467±0.2°, 20.705±0.2°, 24.929±0.2°, 27.101±0.2°, 17.192±0.2°, 19.778±0.2°, 22.799±0.2°, 23.590±0.2° and 27.416±0.2°; and the polymorph IV is polymorph IV of ethanol solvate of the 1/1 p-toluenesulfonate of compound I (1:1:1), and the polymorph IV comprises the following characteristic peaks in X-ray powder diffraction pattern selected from the group consisting of: 20.961±0.2°, 18.277±0.2°, 9.273±0.2°, 15.812±0.2°, 24.674±0.2°, 25.246±0.2° and 27.552±0.2°.

2. The method of claim 1, wherein the subject has a cancer.

3. The method of claim 1, wherein the subject is a human.

4. The method of claim 1, wherein the polymorph is polymorph I of the 1/1 p-toluenesulfonate of compound I, and the polymorph I has a DSC pattern as shown in FIG. 1b.

5. A method for preparing a pharmaceutical composition for inhibiting phosphokinase, comprising:
(a) mixing a polymorph of a pharmaceutically acceptable p-toluensulfonate salt of compound I with a pharmaceutically acceptable excipient, thereby forming the pharmaceutical composition,

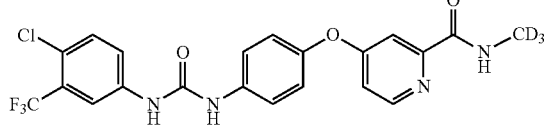

I the polymorph being selected from the group consisting of polymorph I, III, and V of the p-toluenesulfonate of compound I, and polymorph IV of ethanol solvate of the p-toluenesulfonate of compound I, wherein:

the polymorph I is polymorph I of the 1/1 p-toluenesulfonate of compound I, and the polymorph I comprises the following characteristic peaks in X-ray powder diffraction pattern:

| Peak No. | 2θ(°) |
|---|---|
| 1 | 4.397 |
| 2 | 10.643 |
| 3 | 11.068 |
| 4 | 11.608 |
| 5 | 12.193 |
| 6 | 12.791 |
| 7 | 13.182 |
| 8 | 14.759 |
| 9 | 15.981 |
| 10 | 16.636 |
| 11 | 17.821 |
| 12 | 18.764 |
| 13 | 19.360 |
| 14 | 20.030 |
| 15 | 20.407 |
| 16 | 20.782 |
| 17 | 21.472 |
| 18 | 22.076 |
| 19 | 22.833 |
| 20 | 23.345 |
| 21 | 23.640 |
| 22 | 24.472 |
| 23 | 25.005 |
| 24 | 25.355 |
| 25 | 25.968 |
| 26 | 26.578 |
| 27 | 26.917 |
| 28 | 27.292 |
| 29 | 28.101 |
| 30 | 28.535 |
| 31 | 29.524 |
| 32 | 29.837 |
| 33 | 30.785 |
| 34 | 31.084 |
| 35 | 31.538 |
| 36 | 31.974 |
| 37 | 33.169 |
| 38 | 33.863 |
| 39 | 34.180 |
| 40 | 35.695 |
| 41 | 37.021 |
| 42 | 38.420 |
| 43 | 39.213 |
| 44 | 41.124 | and the polymorph I has a maximum peak of 237.7° C. in differential scanning calorimetry pattern;

the polymorph III is polymorph III of the 1/1 p-toluenesulfonate of compound I, and the polymorph III comprises the following characteristic peaks in X-ray powder diffraction pattern: 19.858±0.2°, 25.896±0.2°, 17.726±0.2°, 19.325±0.2° and 21.575±0.2°;

the polymorph V is polymorph V of the 1/2 p-toluenesulfonate of compound I, and the polymorph V comprises the following characteristic peaks in X-ray powder diffraction pattern: 13.423±0.2°, 13.974±0.2°, 20.467±0.2°, 20.705±0.2°, 24.929±0.2°, 27.101±0.2°, 17.192±0.2°, 19.778±0.2°, 22.799±0.2°, 23.590±0.2° and 27.416±0.2°; and the polymorph IV is polymorph IV of ethanol solvate of the 1/1 p-toluenesulfonate of compound I (1:1:1), and the polymorph IV comprises the following characteristic peaks in X-ray powder diffraction pattern selected from the group consisting of: 20.961±0.2°, 18.277±0.2°, 9.273±0.2°, 15.812±0.2°, 24.674±0.2°, 25.246±0.2° and 27.552±0.2°.

6. The method of claim 5, wherein the phosphokinase is raf kinase.

7. The method of claim 5, wherein the polymorph is polymorph I of the 1/1 p-toluenesulfonate of compound I, and the polymorph I has a DSC pattern as shown in FIG. 1b.

* * * * *